United States Patent [19]

Levine

[11] Patent Number: 5,843,712

[45] Date of Patent: Dec. 1, 1998

[54] SINDBIS VIRUS EXPRESSION SYSTEM FOR RECOMBINANT ANTIBODY PRODUCTION

[75] Inventor: Beth Cindy Levine, Scarborough, N.Y.

[73] Assignee: The Trustees of Columbia University in the City of New York, New York, N.Y.

[21] Appl. No.: 659,567

[22] Filed: Jun. 6, 1996

[51] Int. Cl.[6] .............................. C12P 21/06; C12P 21/04; C12N 15/00; C12N 7/00

[52] U.S. Cl. ....................... 435/69.1; 435/69.6; 435/70.1; 435/172.3; 435/235.1; 435/326; 435/348

[58] Field of Search .............................. 435/172.3, 320.1, 435/69.1, 69.6, 240.1, 240.2, 325, 326, 328, 346, 348, 240.26, 240.27, 70.1, 235.1

[56] References Cited

U.S. PATENT DOCUMENTS 5,217,879  6/1993  Huang et al. ........................... 435/69.1

OTHER PUBLICATIONS

Bowdish, K., et al. (1991) "Yeast expression of a catalytic antibody with chorismate mutase activity." *J. Biol. Chem.* 266: 11901–11908 (Exhibit C).

Carroll, A.R., et al. (1992) "Synthesis and secretion of a functional antibody in a vaccinia virus expression system." *Molecular Immunol.* 29:821–827 (Exhibit D).

Coloma, M. J., et al. (1992) "Novel vector for the expression of antibody molecules using variable regions generated by polymerase chain reaction." *J. Immunol. Methods* 152:89–104 (Exhibit E).

Cheng, E.H.-Y., et al. (1996) "Bax–independent inhibition of apoptosis By Bcl–X." *Nature* 379:554–556 (Exhibit F).

Hasemann, C.A. and Capra, J.D. (1990) "High level production of a functional immunoglobulin heterodimer in a baculovirus expression system." *Proc. Natl. Acad. Sci USA* 87:3942–3946 (Exhibit G).

Hahn, C.S., et al. (1992) "Infectious Sindbis virus transient expression vectors for studying antigen processing and presentation." *Proc. Natl. Acad. Sci. USA* 89: 2679–2683 (Exhibit H).

Hertz, J. and Huang, H.V. (1992) "Utilization of heterologous alphavirus junction sequences as promoters by Sindbis virus." *J. Virol.* 66: 491–496 (Exhibit I).

Horwitz, A.H., et al. (1988) "Secretion of functional antibody and Fab fragment from yeast cells." *Proc. Natl. Acad. Sci. USA* 85:8678–8682 (Exhibit J).

Jiang, W., et al. (1995) "Intracellular interference of tick–borne flavivirus infection by using a single–chain antibody fragment delivered by recombinant Sindbis virus." *J. Virol.* 69:1044–1049 (Exhibit K).

Levine, B., et al. (1996) "Bcl–2 protects mice against fatal alphavirus encephalitis." *Proc. Natl. Acad. Sci. USA* 93:4810–4815 (Exhibit L).

Nesbit, M., et al. (1992) "Production of a functional monoclonal antibody recognizing human colorectal carcinoma cells from a baculovirus expression system." *J. Immunol. Method* 151:201–208 (Exhibit M).

(List continued on next page.)

*Primary Examiner*—Jasemine C. Chambers
*Assistant Examiner*—Deborah J. R. Clark
*Attorney, Agent, or Firm*—John P. White; Cooper & Dunham LLP

[57] ABSTRACT

This invention provides a method of expressing a multimeric polypeptide. This invention also provides a method of expressing biologically active recombinant antibodies. This invention also provides an expression cell line capable of producing multimeric polypeptides or biologically active recombinant antibodies. This invention also provides methods of producing biologically active recombinant antibodies or multimeric polypeptides. This invention also provides a transgenic animal comprising the expression cell line capable of producing biologically active recombinant antibodies or multimeric polypeptides. Also, this invention provides a method for preventing infectious diseases associated with arthropods.

12 Claims, 11 Drawing Sheets

OTHER PUBLICATIONS

Piper, R.C., et al. (1992) "The efficient intracellular sequestration of the insulin–regulatable glucose transporter (GLUT–4) is conferred by the $NH_2$ terminus." *J. Cell Biol.* 117:729–743 (Exhibit N).

Poul, M.A., et al. (1995) "Cassette baculovirus vectors for the production of chimeric, humanized, or human antibodies in insect cells." *Eur. J. Immunol.* 25:2005–2009 (Exhibit O).

Schlesinger, S. (1993) "Alphaviruses—vectors for the expression of heterologous genes." *TIBTECH* 11: 18–22 (Exhibit P).

Xiong, C., et al. (1989) "Sindbis virus: an efficient, broad host range vector for gene expression in animal cells." *Science* 243: 1188–1191 (Exhibit Q).

FIG. 1A
SIN/R6H
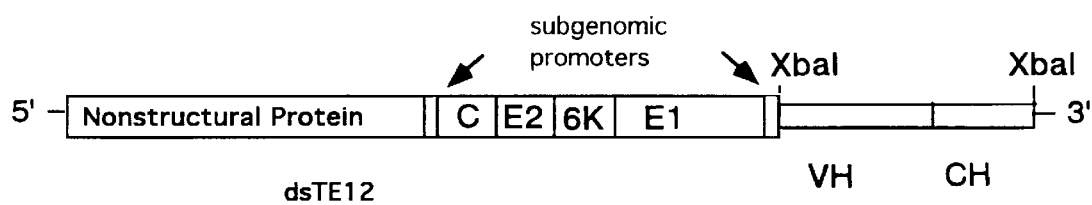
SIN/R6L
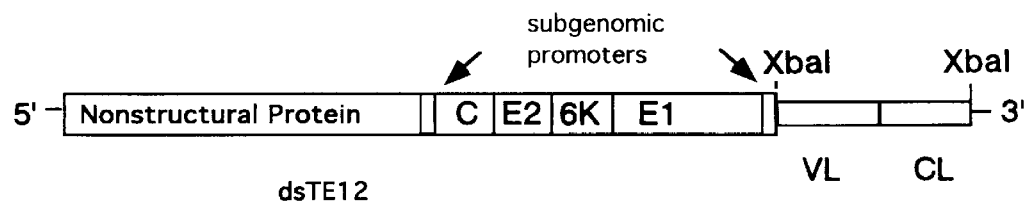

FIG. 2A

| | |
|---|---|
| 1 | ATGGATTTTCAAGTGCAGATTTTCAGCTTC<br>MetAspPheGlnValGlnIlePheSerPhe |
| 31 | CTGCTAATCAGTGTCACAGTCATAATGTCC<br>LeuLeuIleSerValThrValIleMetSer |
| 61 | AGAGGAGAAAATGTGCTCACCCAGTCTCCA<br>ArgGlyGluAsnValLeuThrGlnSerPro |
| 91 | GCAATAATGGCTGCCTCTCTGGGGCAGAAG<br>AlaIleMetAlaAlaSerLeuGlyGlnLys |
| 121 | GTCACCATGACCTGCAGTGCCAGCTCAAGT<br>ValThrMetThrCysSerAlaSerSerSer |
| 151 | GTAAGTTCCAGTTACTTGCACTGGTACCAG<br>ValSerSerSerTyrLeuHisTrpTyrGln |
| 181 | CAGAAGTCAGGCGCTTCCCCCAAACCCTTG<br>GlnLysSerGlyAlaSerProLysProLeu |
| 211 | ATTCATAGGACATCCAACCTGGCTTCTGGA<br>IleHisArgThrSerAsnLeuAlaSerGly |
| 241 | GTCCCAGCTCGCTTCAGTGGCAGTGGGTCT<br>ValProAlaArgPheSerGlySerGlySer |
| 271 | GGGACCTCTTACTCTCTCACAATCAGCAGC<br>GlyThrSerTyrSerLeuThrIleSerSer |
| 301 | GTGGAGGCTGAAGATGATGCAACTTATTAC<br>ValGluAlaGluAspAspAlaThrTyrTyr |
| 331 | TGCCAGCAGTGGAGTGGTTACCCATTCACG<br>CysGlnGlnTrpSerGlyTyrProPheThr |
| 361 | TTCGGTGCTGGGACCAAGCTGGAGCTGAAA<br>PheGlyAlaGlyThrLysLeuGluLeuLys |

FIG. 2B

```
  1    ATGGAATGGAGCTGGGTCTTTATCTTTCTC
       MetGluTrpSerTrpValPheIlePheLeu

31    TTGTCAGTAACTGCAGATGTCCACTCCCAG
       LeuSerValThrAlaAspValHisSerGln

61    GTCCAGTTGCAGGAGTCTGGAGGTGAGCTG
       ValGlnLeuGlnGluSerGlyGlyGluLeu

91    GTAAGGCCTGGGACTTCAGTGAAGATATCC
       ValArgProGlyThrSerValLysIleSer

121    TGCAAGGCTTCTGGCTACACCTTCACTAAT
       CysLysAlaSerGlyTyrThrPheThrAsn

151    TACTGGCTAGGTTGGGTAAAGCAGAGGCCT
       TyrTrpLeuGlyTrpValLysGlnArgPro

181    GGACATGGACTTGAGTGGATTGGAGATATT
       GlyHisGlyLeuGluTrpIleGlyAspIle

211    TACCCTGGAGGTGATTATACTAATTACAAT
       TyrProGlyGlyAspTyrThrAsnTyrAsn

241    GAGAAGTTCAAGGGCAAGGCCACACTGACT
       GlluLysPheLysGlyLysAlaThrLeuThr

271    GCAGACACATCCTCCAGCACTGCCCACATG
       AlaAspThrSerSerSerThrAlaHisMet

301    CAGCTCAGTAGCCTGACATCTGAGGACTCT
       GlnLeuSerSerLeuThrSerGluAspSer

331    GCTGTCTATTTCTGTGCAATATTTCATTAC
       AlaValTyrPheCysAlaIlePheHisTyr

361    TCCGGCTACAGGTACTTCGATGTCTGGGGC
       SerGlyTyrArgTyrPheAspValTrpGly

391    GCAGGGACCACGGTCACCGTCTCCTCAGCT
       AlaGlyThrThrValThrValSerSerAla

421    AGC
       Ser
```

FIG. 8A

```
<-------- J_κ -------------------->  <-- ------>
                                      Splicing
   96       99   101            107   signal
LeuThrPheGlyAlaGlyThrLysLeuGluLeuLys
ctcacgttcggtgctggaccaagctggagctgaaa  cgtaagtacac                  J5
          acgaccctggttcgacctcgacttt  gcattcaGCtg tct 5'   primer MJ_κ5 (anti-sense 39mer)
                                           Sal I PheThrPheGlySerGlyThrLysLeuGluIleLys
TtcacgttcggCTcGgggacaCaAaagTtggaAAtAaaa cgtaagtagac                  J4
       ccgagccctgtttcaacctttatttt       gcattcaGctg tct 5'   primer MJ_κ4 (anti-sense 41mer)

TyrThrPheGlyGlyGlyThrLysLeuGluIleLys
TAcacgttcggAgGGggaccaagctggaaAAtAaaa  cgtaagtagtc                  J2
        ctccccccctggttcgacctttatttt   gcattcaGcTg tct 5'   primer MJ_κ2 (anti-sense 40mer)

TrpThrPheGlyGlyGlyThrLysLeuGluIleLys
TGGacgttcggtgGAggCaccaagctggaAAtCaaa  cgtaagtagaa                  J1
       cacctccgtggttcgacctttagttt     gcattcaGctg tct 5'   primer MJ_κ1 (anti-sense 40mer)

ggtgctggaccaagctggagctgaaa                              Sense consensus of active mouse J_κ
   atga  c   a  t    aa c
              g            a
   c  g
```

FIG. 8B

```
                    <------------------ J_H ------------------>            <----- HuY -
                              104    106               113                   114
J1                    TyrTrpTyrPheAspValTrpGlyAlaGlyThrThrValThrValSerSer     AlaSer . .   \\
                      tactggtacttcgatgtctggggcgcaggaccaccgtcaccgtctcctca     gcctcc------\\
                                              Aca in C57BL & C58/J           AlaSer       engineered
                                              Thr                            gcTAGc
                                                                             NheI
Primer MJH1(anti-sense, 35mer)           gtccctggtgccagtggcacagaggagt        cgatcg tta 5'

J2                    TyrPheAspTYRTrpGlyGLNGlyThrThrLEUThrValSerSer
                      tactTTgaCTActgggGCCAaggCaccacTCtcacAgtctcctca
Primer MJH2(anti-sense, 37mer)         ggttccgtggtgagagtgtcagaggagt          cgatcg tta 5'

J3                    TrpPheALATYRTrpGlyGLNGlyThrLEUValThrValSerALA
                      tGGttTgCtTActgggGCCAagggaCTCTggtcacTgtctcTGca
Primer MJH3(anti-sense, 37mer)          ggttccctgagaccagtgacagagacgt         cgatcg tta 5'

J4                    TyrTYRALAMETAspTYRTrpGlyGLNGlyThrSERValThrValSerSer
                      tactATGCTAtGgacTActgggGTCAaggaAccTcAgtcaccgtctcctca
Primer MJH4(anti-sense, 38mer)         cagttccttggagtcagtggcagaggagt         cgatcg tta 5'
```

SINDBIS VIRUS EXPRESSION SYSTEM FOR RECOMBINANT ANTIBODY PRODUCTION

The invention disclosed herein was made with Government support under Grant No. K08AI01217-01 from the National Institutes of Health of the United States Department of Health and Human Services. Accordingly, the U.S. Government has certain rights in this invention.

BACKGROUND OF THE INVENTION

Throughout this application, various publications are referenced by author and date. Full citations for these publications may be found listed alphabetically at the end of the specification immediately preceding Sequence Listing and the claims. The disclosures of these publications in their entireties are hereby incorporated by reference into this application in order to more fully describe the state of the art as known to those skilled therein as of the date of the invention described and claimed herein.

Within the past two decades, several different expression systems have been developed for the production of genetically engineered antibodies. Bacterial expression is useful for the production of large quantities of antibody fragments, including Fv's, Fab's, and ScFv's, but as of yet, cannot be used for the production of native antibody molecules (Skerra and Pluckthun, 1988, Huse et al., 1989, Sastry et al., 1989, Ward et al., 1989). While yeasts cells have been shown to secrete fully assembled antibodies with antigen-binding activity (Horwitz et al., 1988, Bowdish et al., 1991), the yield of antibody produced is low and the ability of such antibodies to fix human complement is impaired by a high mannose-type oligosaccharide attached to an N-linked glycosylation site (Horwitz et al., 1988). Expression of functional mouse and humanized antibodies has been demonstrated in insect cells (Hasemann and Capra, 1990, Nesbit et al, 1992, Poul et al., 1995), but it is still unclear whether insect cell-specific glycosylation will affect biologic activity. Furthermore, antibodies produced in yeast or insect cells may have increased immunogenicity and more rapid clearance by asialo-oligosaccharide and mannose receptor-binding cells. In contrast, the expression of recombinant antibodies in mammalian cells offers great advantages with respect to post-translational modifications, stability, immunogenicity, and yields. However, one major disadvantage of many mammalian expression systems is the need to select stable transfectant clones, a time-consuming process. Sindbis virus vectors which have already been used successfully for the transient expression of many heterologous proteins in mammalian cells (Schlesinger, 1993; Huang, et al., 1993), offer a potentially powerful tool for the rapid production of genetically engineered antibodies. Previous studies have demonstrated that a Sindbis virus vector expresses a functionally active ScFv that neutralizes tick-borne encephalitis virus (Jiang et al., 1994; Jiang et al., 1995).

Sindbis virus, the prototype alphavirus, is a single-stranded positive RNA virus that has a broad range of susceptible host cells. In mice, Sindbis virus replicates predominantly in neurons (Jackson et al., 1987) and produces an age-dependent fatal encephalitis (Johnson et al., 1972). The Sindbis virus genome is 11,703 nucleotides; the 5' two thirds encodes the nonstructural proteins, which are translated as polyproteins from a messenger RNA that is indistinguishable from the virion RNA (full-length genomic 49S RNA). These precursors are cleaved post-translationally to produce four nonstructural proteins, nsP1, nsP2, nsP3, and nsP4 which function as the replicase/transcriptase for the virus. The 3' one third of the genome encodes the structural proteins, which are translated from a 26S subgenomic mRNA as a polyprotein that is cleaved co- and post-translationally to form five polypeptides—capsid, E3, E2, 6K, E1. PE2 is the precursor form of E2 and consists of both E3 and E2. E2 is the major attachment protein and contains the epitopes that elicit the most potent neutralizing antibodies. Neutralizing and nonneutralizing MAbs to E2 prevent fatal Sindbis virus encephalitis (Schmaljohn et al., 1982, Stanley et al., 1986). In addition, MAbs to two different neutralizing epitopes on the E2 glycoprotein down-regulate intracellular Sindbis virus replication in persistently infected scid mice and cultured dorsal root ganglion neurons (Levine et al., 1991, Ubol et al., 1995). E3 is thought to serve as a signal sequence for E2 but is cleaved by a cathepsin-type protease (rather than signal peptidase) late in replication (possibly in the Golgi). 6K is thought to serve as a signal sequence for E1. Three of these polypeptides, capsid protein (C) and the envelope glycoproteins E1 and E2 are found on the mature Sindbis virus virion. Cytoplasmic "cytopathic vacuoles" which are modified endosomes and lysosomes constitute the sites of viral RNA synthesis, translation of structural proteins, and assembly of nucleocapsid. E1 (49 kDa) and E2 (47 kDa) are transmembrane proteins that associate with each other soon after synthesis to form stable, noncovalently linked heterodimers. These heterodimers trimerize, are translocated through the Golgi, and move to the cell membrane to form columnar knobs with a T=4 icosahedral lattice on the surface of the mature virion. The E1–E2 heterodimer proteins are responsible for virus attachment to the cell surface (E2) and mediate acid-dependent fusion of the virion with the endosomal membrane (E1). Both E1 and E2 elicit neutralizing and protective antibody responses and are important determinants of neurovirulence.

Sindbis virus provides an ideal model for the study of host defense mechanisms against acute viral encephalitis for several reasons: 1) Sindbis virus provides an excellent experimental animal model of acute encephalitis, which closely parallels human disease caused by related members of the alphavirus family, Eastern and Western equine encephalitis viruses (important causes of arthropod-borne encephalitis in the US). In addition, many biologic similarities exist between alphaviruses and other arthropod-borne viruses, such as Japanese encephalitis virus (a Flavivirus) which is the most important cause of encephalitis worldwide. 2) Sindbis virus infection produces fatal encephalitis in neonatal mice, but self-limited, clinically silent encephalitis in adult mice, thus permitting the investigation of host factors (present in adult, but not neonatal mice) that are critical to successful recovery from viral infection. 3) A biologically relevant tissue culture model using cultured neurons has been established in which two host defense mechanisms previously described to be important in vivo—the ability of antiviral antibodies to restrict viral gene expression and the avoidance of a lytic phenotype—are reproduced in vivo. 4) Complete sequence information of the viral genome is available as well as full length cDNA clones from which infectious viral RNA can be transcribed in vitro, thus greatly facilitating genetic manipulation and analysis of the molecular interactions between Sindbis virus and host defense factors.

SUMMARY OF THE INVENTION

This invention provides a recombinant Sindbis viral vector comprising a nucleic acid molecule encoding a transcription unit which comprises a nucleic acid encoding immunoglobulin heavy chain protein under the control of a promoter downstream of the Sindbis virus structural genes.

This invention also provides a recombinant Sindbis viral vector comprising a nucleic acid molecule encoding a transcription unit which comprises a nucleic acid encoding immunoglobulin light chain protein under the control of a promoter downstream of the Sindbis virus structural genes.

This invention also provides an expression cell line comprising the recombinant Sindbis viral vectors described above.

This invention also provides a method of producing a Sindbis virus/immunoglobulin heavy chain chimeric virus which comprises a nucleic acid molecule encoding a transcription unit comprising a nucleic acid which encodes immunoglobulin heavy chain protein This invention also provides a Sindbis virus/immunoglobulin heavy chain chimeric virus comprising a nucleic acid molecule encoding a transcription unit comprising a nucleic acid which encodes immunoglobulin heavy chain protein produced by the method described above.

This invention also provides a method of producing a Sindbis virus/immunoglobulin light chain chimeric virus comprising a nucleic acid molecule encoding a transcription unit comprising a nucleic acid which encodes immunoglobulin light chain protein.

This invention also provides a Sindbis virus/immunoglobulin light chain chimeric virus comprising a nucleic acid molecule encoding a transcription unit comprising a nucleic acid which encodes immunoglobulin light chain protein produced by the method described above.

This invention also provides a method of expressing biologically active recombinant antibodies.

This invention also provides an expression cell line capable of producing biologically active recombinant antibodies.

This invention also provides several methods of producing biologically active recombinant antibodies.

This invention also provides a method of obtaining a polypeptide in purified form.

This invention also provides a transgenic animal comprising the expression cell line capable of producing biologically active recombinant antibodies.

This invention also provides a method for immunizing arthropods.

BRIEF DESCRIPTION OF THE FIGURES

FIGS. 1A and 1B.

1A. Schematic diagram of Sindbis virus/R6 cDNA clones. The entire heavy chain (VH and CH) and light chain (VK and CK) R6 genes were separately cloned into double subgenomic Sindbis virus vectors (strain dsTE12 [Levine et al., 1996) downstream of the second subgenomic promoter to generate the plasmids, Sindbis virus/R6H and Sindbis virus/R6L, respectively.

1B. Schematic representation of the strategy used for the cloning of R6 heavy and light chain genes and the construction of recombinant Sindbis virus/R6 chimeric viruses. R6 hybridoma cDNA was reverse transcribed from RNA and used as template for the PCR amplification of heavy and light chain genes. R6 heavy and R6 light chain genes were cloned into the double subgenomic Sindbis virus vectors to construct Sindbis virus/R6H and Sindbis virus/R6L as depicted in FIG. 1A. Infectious chimeric virus stock were made by transfecting BHK-21 cells with in vitro transcribed RNA from recombinant Sindbis virus/R6H and Sindbis virus/R6L clones.

FIGS. 2A and 2B 2A. cDNA sequence (Sequence ID No.: 1) and translated amino acid sequence (Sequence ID No.: 2) for VH of the anti-Sindbis virus E2 MAb from hybridoma R6.

2B. cDNA sequence (Sequence ID No.: 3) and translated amino acid sequence (Sequence ID No.: 4) for Vk of the anti-Sindbis virus E2 MAb from hybridoma R6. Numbering is by sequential nucleotides.

Figure 3A:
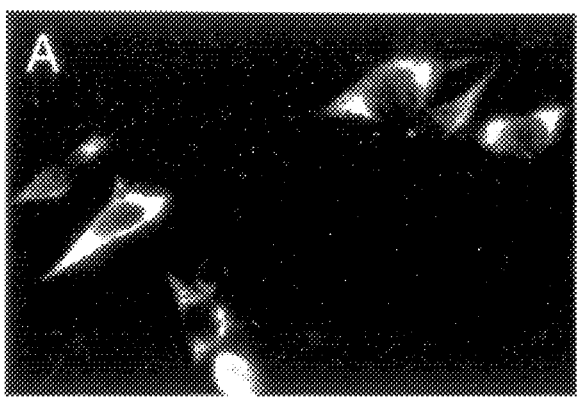
Figure 3B:
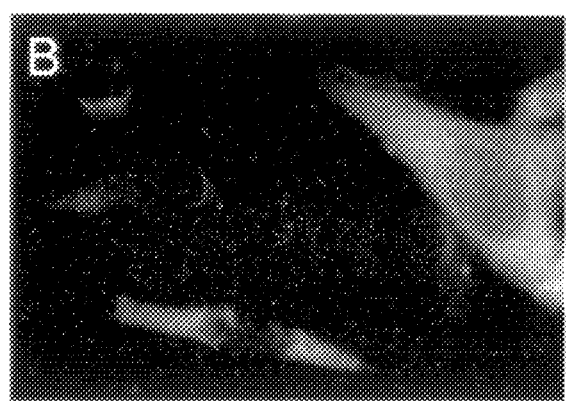

FIGS. 3A and 3B

3A. Immunofluorescent staining of R6 heavy chains expressed in BHK-21 cells.

3B. Immunofluorescent staining of R6 light chains expressed in BHK-21 cells.

FIG. 4

IgG quantitation curve of assembled recombinant R6 in the supernatant of BHK-21 cells co-infected with Sindbis virus/R6H and Sindbis virus/R6L.

FIG. 5

Western blot detection of IgG proteins from recombinant R6 expressing BHK-21 cells (Lane 2) or R6 purified by ascites (Lane 1). H refers to heavy chains; L refers to light chains.

FIG. 6

ELISA analysis of the E2 binding activity of recombinant R6 and R6 purified from ascites.

FIG. 7

The effect of recombinant R6 and R6 purified from ascites on the clearance of infectious Sindbis virus from the brains of persistently infected scid mice.

Results are presented as the mean ±S.E. for three mice per treatment group. FIGS. 8A and 8B 8A. Sequences of the four active mouse $J_K$ and the PCR primers with Sal I site and the intact splicing signal [Sense consensus of active mouse $J_K$ (Sequence ID No.: 5) ; primer $MJ_K1$ (Sequence ID No.: 6); nucleotide sequence of J1 (Sequence ID No.: 7); amino acid sequence of J1 (Sequence ID No.:8); primer $MJ_K2$ (Sequence ID No.: 9); nucleotide sequence of J2 (Sequence ID No.: 10); amino acid sequence of J2 (Sequence ID No.: 11); primer $MJ_K4$ (Sequence ID No.: 12); nucleotide sequence of J4 (Sequence ID No.: 13); amino acid sequence of J4 (Sequence ID No.: 14) ; primer $MJ_K5$ (Sequence ID No.: 15); nucleotide sequence of J5 (Sequence ID No.: 16); amino acid sequence of J5 (Sequence ID No. 17)].

8B. Sequences of the four active mouse $J_H$ and the PCR primers with the Nhe I site [primer $MJ_H1$ (Sequence ID No.: 18); nucleotide sequence of J1 (Sequence ID No.: 19) ; amino acid sequence of J1 (Sequence ID No.: 20); primer $MJ_H2$ (Sequence ID No.: 21); nucleotide sequence of J2 (Sequence ID No.: 22) ; amino acid sequence of J2 (Sequence ID No.: 23) primer $MJ_H3$ (Sequence ID No.: 24); nucleotide sequence of J3 (Sequence ID No.: 25); amino acid sequence of J3 (Sequence ID No.: 26); primer $MJ_H4$ (Sequence ID No.: 27); nucleotide sequence of J4 (Sequence ID No.: 28); amino acid sequence of J4 (Sequence ID No.: 29)].

DETAILED DESCRIPTION OF THE INVENTION

Throughout this application, references to specific nucleotides are to nucleotides present on the coding strand of the nucleic acid. The following standard abbreviations are used throughout the specification to indicate specific nucleotides:

C=cytosine A=adenosine

T=thymidine G=guanosine

A "gene" means a nucleic acid molecule, the sequence of which includes all the information required for the normal regulated production of a particular protein, including the structural coding sequence, promoters and enhancers.

The nucleic acids of the subject invention also include nucleic acids or oligonucleotides coding for polypeptide analogs, fragments or derivatives which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These nucleic acids or oligonucleotides include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

The nucleic acids described and claimed herein are useful for the information which they provide concerning the amino acid sequence of the polypeptide and as products for the large scale synthesis of the polypeptide by a variety of recombinant techniques. The molecule is useful for generating new cloning and expression vectors, transformed and transfected prokaryotic and eukaryotic host cells, and new and useful methods for cultured growth of such host cells capable of expression of the polypeptide and related products.

In order to facilitate an understanding of the material which follows, certain frequently occurring methods and/or terms are best described in Sambrook, et al., 1989.

The invention provides for a recombinant Sindbis viral vector comprising a nucleic acid molecule encoding a transcription unit which comprises a nucleic acid encoding immunoglobulin heavy chain protein under the control of a promoter downstream of the Sindbis virus structural genes.

The nucleic acid encoding immunoglobulin heavy chain protein may be DNA or RNA, specifically cDNA, genomic DNA or mRNA. Specifically, the nucleic acid is derived from genes which encode an antibody to the Sindbis E2 envelope glycoprotein.

This invention also provides for a recombinant Sindbis viral vector comprising a nucleic acid molecule encoding a transcription unit which comprises a nucleic acid encoding immunoglobulin light chain protein under the control of a promoter downstream of the Sindbis virus structural genes.

The nucleic acid encoding immunoglobulin light chain protein may be DNA or RNA, specifically cDNA, genomic DNA or mRNA. Specifically, the nucleic acid is derived from genes which encode an antibody to the Sindbis E2 envelope glycoprotein.

As used in this application, "recombinant Sindbis viral vector" means a Sindbis virus which does not occur naturally and has been engineered to contain a promoter downstream of the Sindbis native structural genes. Specifically, the recombinant Sindbis viral vector includes a nucleic acid encoding either the immunoglobulin heavy or light chain proteins which are operatively linked to above-described promoter. Methods of engineering a Sindbis virus to form a recombinant Sindbis viral vector are well known in the art (Huang, et al. 1993) using recombinant technology.

As used in this application, "transcription unit" means a sequence of nucleotides comprising a nucleic acid which encodes either an immunoglobulin heavy chain protein or an immunoglobulin light chain protein which is operatively linked to a promoter downstream of the Sindbis native viral structural genes.

This invention also provides an expression cell line comprising the Sindbis viral vectors described above. The expression cell line is eukaryotic. Further the eukaryotic expression cell line may be a mammalian cell. Also, the eukaryotic expression cell may be from an arthropod. Suitable cells include, but are not limited to, prokaryotic or eukaryotic cells, e.g. bacterial cells (including gram positive cells), yeast cells, fungal cells, insect cells, and animals cells. Numerous mammalian cells may be used as hosts, including, but not limited to, the mouse fibroblast cell NIH3T3, CHO cells, HeLa cells, Ltk$^{31}$ cells, Cos cells, etc.

As used in this application, "an expression cell line" is a cell capable of expressing protein encoded from nucleic acids infected into the cell.

As used in the subject application, the term "antibody" includes, but is not limited to, both naturally occurring and non-naturally occurring antibodies encoded by a nucleic acid. Specifically, the term "antibody" includes polyclonal and monoclonal antibodies, and binding fragments thereof. Furthermore, the term "antibody" includes chimeric antibodies, wholly synthetic antibodies and fragments thereof which are capable of carrying the biological function of the antibody. Antibodies are assembled from proteins which are encoded by immunoglobulin heavy chain genes and immunoglobulin light chain genes.

This invention also provides a method of producing a chimeric Sindbis virus capable of expressing immunoglobulin heavy chain protein which comprises: (a)obtaining the nucleic acid which encodes immunoglobulin heavy chain protein; (b) operatively linking the obtained nucleic acid to a Sindbis cDNA clone which is capable of being transcribed and contains elements, including structural genes, required for viral replication so as to form a chimeric Sindbis virus cDNA clone; (c) transcribing the chimeric Sindbis virus cDNA clone of step (b); (d) isolating the transcript of step (c); (e)transfecting the isolated transcripts of step (d) into a eukaryotic cell; and (f) culturing the cell of step (e) so as to produce a chimeric Sindbis virus immunoglobulin capable of expressing immunoglobulin heavy chain protein.

Methods of linking nucleic acid to cDNA clones, transcribing these clones, and isolating the resulting transcripts are well-known in the art (Sambrook, et al. 1989). Methods of transfecting cells with the transcripts of cDNA clones and culturing them are also well-known in the art.

As used in this application, "chimeric Sindbis virus" means a Sindbis virus which contains heterologous coding sequences downstream of a promoter which is downstream of the native Sindbis viral structural genes.

As used in this application, "heterologous coding sequences" means a nucleic acid, not naturally in Sindbis viruses, encoding one component of a biologically active polypeptide. In a specific embodiment, the nucleic acid encodes either an immunoglobulin heavy chain protein or an immunoglobulin light chain protein.

As used in this application, "Sindbis virus cDNA clone" means cDNA clones of the Sindbis virus genome which encode biologically active Sindbis virus. These cDNA clones are constructed using well-known recombinant DNA technology and methods. A specific embodiment of a Sindbis virus cDNA clone is designated dsTE12 (Levine b, et al. 1996).

As used in this application, "chimeric Sindbis virus cDNA clone" means a Sindbis virus cDNA clone comprising heterologous coding sequences downstream of a promoter which is downstream of the native Sindbis viral structural genes and is capable of being transcribed into RNA.

Methods of obtaining nucleic acids encoding specific polypeptides, e.g. antibodies or components of polypeptides are well known in the art. One skilled in the art knows that one can isolate nucleic acids from various sources, e.g. phage libraries, cDNA libraries or genomic DNA libraries. A specific means of obtaining the nucleic acids of the above-described step is by: (i) obtaining hybridoma cells expressing a specific monoclonal antibody, (ii) isolating mRNAs from said hybridoma cells, (iii) generating cDNAs of the isolated mRNAs from step (ii), and (iv) isolating cDNAs encoding immunoglobulin heavy chain protein so as to obtain a nucleic acid which encodes immunoglobulin heavy chain protein. One could isolate the cDNAs encoding immunoglobulin heavy chain protein of step (iv) by amplifying the cDNAs generated in step (iii) and detecting the presence of cDNAs encoding immunoglobulin heavy chain protein. One means of amplifying cDNAs is using the polymerase chain reaction (PCR). This method is well-known in the art.

This invention also produces a chimeric Sindbis virus capable of expressing immunoglobulin heavy chain protein and produced by the above-described method.

This invention also provides a method of producing a chimeric Sindbis virus comprising a nucleic acid molecule capable of expressing immunoglobulin light chain protein which comprises: (a) obtaining the nucleic acid which encodes immunoglobulin light chain protein; (b) operatively linking the obtained nucleic acid to a Sindbis cDNA clone which is capable of being transcribed and contains elements, including structural genes, required for viral replication so as to form a chimeric Sindbis virus cDNA clone; (c) transcribing the chimeric Sindbis virus cDNA clone of step (b); (d) isolating the transcript of step (c) ; (e) transfecting the isolated transcripts of step (d) into a eukaryotic cell; and (f)culturing the cell of step (e) so as to produce a chimeric Sindbis virus immunoglobulin capable of expressing immunoglobulin light chain protein.

A specific means of obtaining the nucleic acids of step (a) comprises: (i) obtaining hybridoma cells expressing a specific monoclonal antibody, (ii) isolating mRNAs from the said hybridoma cells, (iii) generating cDNAs of the isolated mRNAs from step (ii), and (iv) isolating cDNAs encoding immunoglobulin light chain protein so as to obtain a nucleic acid which encodes immunoglobulin light chain protein. One could isolate the cDNAs encoding immunoglobulin light chain protein of step (iv) by amplifying the cDNAs generated in step (iii) and detecting the presence of cDNAs encoding immunoglobulin light chain protein. One specific means of amplifying cDNA is by using the polymerase chain reaction (PCR) This method is well-known in the art.

This invention also provides a chimeric Sindbis virus capable of expressing immunoglobulin light chain protein and produced by the above-described method.

This invention also provides a method of expressing a biologically active multimeric polypeptide which comprises: (a) obtaining nucleic acids which encode individual components of the polypeptide; (b) operatively linking the obtained nucleic acids to Sindbis cDNA clones which are capable of being transcribed and contain elements, including structural genes, required for viral replication so as to form separate and distinct chimeric Sindbis cDNA clones which contain the nucleic acid encoding only one of the components of the polypeptide; (c) transcribing chimeric Sindbis cDNA clones of step (b); (d) isolating the transcripts from step (c); (e) transfecting the isolated transcripts of step (d) into a eukaryotic cell; (f) culturing the transfected cell of step (e) so as to produce separate and distinct chimeric Sindbis viruses which contain the nucleic encoding only one of the components of the polypeptide; (g) isolating chimeric Sindbis viruses encoding each component of the polypeptide in step (f); (h) coinfecting a suitable cell with at least one chimeric Sindbis virus encoding each component of the polypeptide isolated in step (g) permitting expression of each component so as to form a biologically active multimeric polypeptide. Specifically the suitable cell maybe a mammalian cell. Also, the cell may be from an arthropod. Examples of a multimeric polypeptide include, but are not limited to, antibodies or hemoglobin.

In a preferred embodiment, the multimeric polypeptide is a recombinant antibody and is expressed by: (a) obtaining nucleic acids which encode immunoglobulin light chain protein and heavy chain protein; (b) operatively linking the obtained nucleic acids to Sindbis virus cDNA clones which capable of being transcribed and contain elements, including structural genes, required for viral replication so as to form chimeric Sindbis virus cDNA clones, wherein at least one clone comprises nucleic acid encoding immunoglobulin heavy chain and at least another clone comprises nucleic acid encoding immunoglobulin light chain; (c) transcribing the chimeric Sindbis virus cDNA clones of step (b) ; (d) isolating the transcripts from step (c); (e) transfecting the isolated transcripts of step (d) into a eukaryotic cell; (f) culturing the transfected cell of step (e) so as to produce chimeric Sindbis viruses, wherein at least one virus comprises nucleic acid encoding immunoglobulin heavy chain protein and at least another virus comprises nucleic acid encoding immunoglobulin light chain protein; (g) isolating the viral vectors of step (f); (h) coinfecting a suitable cell with the isolated viral vectors of step (g) under conditions so that the cell is capable of expressing biologically active recombinant antibodies. Specifically the suitable cell may be a mammalian cell. Also, the cell may be from an arthropod.

This invention also provides an expression cell line capable of producing biologically active multimeric polypeptides and produced by the above-described method.

This invention also provides an expression cell line capable of producing biologically active recombinant antibodies which comprises chimeric Sindbis virus comprising nucleic acid which encodes the immunoglobulin heavy chain protein and a second chimeric Sindbis virus comprising nucleic acid which encodes the immunoglobulin light chain protein.

This invention also provides a method of producing biologically active recombinant antibodies comprising the above-described recombinant Sindbis viral vectors.

This invention also provides a method of producing biologically active multimeric polypeptides by the using the above-described method for expression of the biologically active multimeric polypeptides.

This invention also provides a method of producing biologically active recombinant antibodies which comprises a chimeric Sindbis virus comprising nucleic acid encoding immunoglobulin heavy chain protein and a second chimeric Sindbis virus comprising nucleic acid encoding immunoglobulin light chain protein.

This invention also provides a method of obtaining a polypeptide in purified form which comprises:(a) introducing a chimeric Sindbis virus comprising nucleic acid encoding immunoglobulin heavy chain protein and a second chimeric Sindbis virus comprising nucleic acid encoding immunoglobulin light chain protein into a suitable host cell; (b) culturing the cell resulting from step (a) so as to produce the polypeptide; (c) recovering the polypeptide produced in step (b); and (d) purifying the polypeptide so recovered.

This invention also provides a transgenic animal comprising an expression cell line capable of expressing a biologically active multimeric polypeptide. In a preferred embodiment, the transgenic animal comprises an expression cell line capable of expressing biologically active recombinant antibodies.

This invention also provides a method of preventing infectious disease associated with arthropods comprising coinfecting arthropod cells with a chimeric Sindbis virus comprising nucleic acid encoding immunoglobulin heavy chain protein and a second chimeric Sindbis virus comprising nucleic acid encoding immunoglobulin light chain protein so as to prevent infectious disease associated with arthropods. In a specific embodiment, the arthropod cells used would include mosquito cells. The coinfection could be either in vivo or in vitro. The chimeric Sindbis viruses would express biologically active recombinant antibodies. These antibodies would neutralize antigens within the arthropod. These antigens could be expressed by viruses, bacteria, yeast and other organisms within the arthropod. Specifically, this method would neutralize antigens derived from, but not limited to, malaria.

Further, the chimeric Sindbis viruses would permanently infect the arthropod so as to produce continuously neutralizing antibodies, thus preventing the arthropod from transmitting antigens to a second organism. In a specific embodiment, the second organism would include, but not limited to, mammals, particularly humans and livestock, e.g. cows, pigs and chickens.

This invention is illustrated in the Experimental Details section which follows. These sections are set forth to aid in an understanding of the invention but are not intended to, and should not be construed to, limit in any way the invention as set forth in the claims which follow thereafter.

EXPERIMENTAL DETAILS

1. Example

Materials and Methods

Cells

Hybridoma cells that secrete an IgG2a MAb to the Sindbis virus E2 envelope glycoprotein, MAb R6, (Olmsted et al., 1984, Olmsted et al., 1986, Schoepp et al., 1993) were grown at 37° C. in Dulbecco's Modified Eagle Medium (DMEM) supplemented with 15% fetal bovine serum, and 1.4 mM L-glutamine. Baby hamster kidney (BHK) cells were grown in DMEM supplemented with 10% fetal calf serum. After virus infections, BHK cells were grown in either DMEM supplemented with 1% fetal calf serum or in serum-free Optimem (Gibco/BRL).

Cloning of immunoglobulin genes

Total RNA was extracted from R6 hybridoma cells with RNA Stat-60 (Tel-Test "B" inc., TX) according to the manufacturer's instructions. Random hexamer priming was used to synthesize cDNA, and variable regions genes were amplified by PCR using degenerate forward primers previously described (Coloma et al., 1992) and reverse primers for the J region of mouse heavy (H) and light (L) chains (FIGS. 8A and 8B). PCR products were cloned into an intermediate cloning vector, pCR™ (Invitrogen, Calif.) and sequenced using the dideoxychain termination method. The resulting sequences were used to design specific forward leader primers for R6 VH and $V_K$ (Sequence ID No.: 30 and Sequence ID No.: 31, respectively) (listed in Table 1). VH and $V_K$ leader primers were used with reverse mouse CH (Sequence ID No:32) (IgG2a) and reverse mouse CK (Sequence ID NO: 33) primers, respectively, to amplify the entire rearranged heavy and light chain genes; Xba I restriction sites were incorporated into all forward and reverse primers. All PCR generated constructs were cloned into pCR™ and sequenced prior to cloning into Sindbis virus cDNA plasmids.

TABLE 1

Primers used for the cloning of R6

| Description | Sequence (5'–3') | |
|---|---|---|
| Forward: | | |
| R6 VH | TACTAGTATCTAGAATGGAATGGAGCTGGGTC | SEQ ID No. 30 |
| R6 VK | ACCTGAGGTCTAGAATGGATTTTCAAGTGCAG | SEQ ID No. 31 |
| Reverse: | | |
| CH | TAACTGAATCTAGATTTACCCGGAGTCCGGGA | SEQ ID No. 32 |
| CK | ACTGGACGTCTAGAACACTCATTCCTGTTGAA | SEQ ID No. 33 |

Xba I restriction site is underlined.

Construction of Sindbis virus/immunoglobulin gene chimeric viruses

The construction of dsTE12 which contains the cDNA of a double subgenomic neurovirulent Sindbis virus clone has been previously described (Levine et al., 1996). The neurovirulent Sindbis virus clone, TE12 was genetically modified to contain a duplicate subgenomic mRNA promoter and unique Xba I cloning site downstream of the Sindbis virus structural genes. A fragment from the double subgenomic clone, TZJSINC (Hertz and Huang, 1992) spanning from the BsiW I site in the E1 gene to the last untranslated nucleotide after the double subgenomic promoter was amplified by polymerase chain reaction (PCR), incorporating a BstE II restriction site into the downstream primer. A fragment from clone TE12 spanning from the beginning of the Sindbis virus 3' nontranslated region to the vector Xho I site was amplified by PCR, incorporating a BstE II site into the upstream primer. The BsiW I-BstE II TZJSINC and BstE II-Xho I TE12 fragments were ligated and inserted into the BsiW I-Xho I sites of clone TE12 to construct a double-subgenomic version of TE12, referred to as dsTE12. The Xba I fragments containing rearranged heavy and light chain genes were excised from pCR™ and cloned into the Xba I site of dsTE12 downstream of the duplicated subgenomic promoter to generate the plasmids, Sindbis virus/R6H and Sindbis virus/R6L, respectively.

Sindbis virus/R6H and Sindbis virus/R6L (1 μg) were linearized with Pvu I and RNA was transcribed in vitro at 37° C. for 60 minutes in a 25 μl reaction containing 1 μg template, 15 units of SP6 RNA polymerase (Gibco/BRL, MD), 30 mM DTT, 160 μM rGTP, 400 μM rATP, rUTP, rCTP, 300 μM methyl $M^7G(5')$ PPP (5') G cap analogue, and 20 units RNAase inhibitor. BHK-21 cells in 35 mm dishes ($5\times10^5$ cells) were transfected with in vitro transcribed RNA mixed with 8 μg of lipofectin (Gibco/BRL) according to the manufacturer's instructions. Twenty four hours after transfection, chimeric virus-containing supernatants were collected and stored in aliquots at −70° C. Titers of virus stocks were determined by plaque assay formation on BHK-21 cells.

Production and purification of recombinant antibodies

BHK-21 cells in 35-mm dishes ($5\times10^5$ cells) were coinfected with Sindbis virus/R6H and Sindbis virus/R6L chimeras at multiplicities of infection (MOI) of 0.1 or 1 plaque-forming unit (PFU)/cell. Supernatants from BHK cells coinfected with Sindbis virus/R6H chain and Sindbis virus/R6L were collected (1 ml) at 8, 12, 16, 18, 24, and 48 hours after infection, and assembled IgG molecules were purified using a protein A/G affinity column (Pierce, Ill.) according to the manufacturer's instructions.

Western blot analysis

Three micrograms of protein A/G-purified IgG were loaded on a 12% SDS-PAGE gel and subsequently transferred to a Hybond nitrocellulose membrane (Amersham, UK). The membrane was first incubated in blocking buffer (1% nonfat dry milk and 1 mM PMSF in TBS) and then reacted at room temperature with peroxidase-conjugated anti-mouse IgG γ chain (1:500, Sigma, Mo.) and anti-mouse κ chain antibody (1:1000, Pharmingen, Calif.). Detection of the γ and κ chains was carried out with enhanced chemiluminescent (ECL) according to manufacturer's instructions (Amersham).

Immunofluorescence staining

BHK-21 cells were grown on glass coverslips and infected with Sindbis virus/R6 chimeras at a MOI of 5. Seven hours after infection, the coverslips were washed with PBS and fixed with cold acetone. For immunofluorescence staining of heavy chains, cells were incubated with rabbit anti-mouse IgG Fc (1:40, Bethyl, Tex.) followed by labeling with fluorescein-conjugated goat anti-rabbit antibody (1:50, Vector Laboratories, Burlingame, Calif.). For immunofluorescence detection of light chain expression, cells were incubated with rhodamine-conjugated anti-mouse κ chain antibody (1:40, Southern Technology, Ala.).

ELISA

The E2 binding activity of secreted recombinant R6 was determined by enzyme-linked immunosorbent assay (ELISA). A Corning 96-well round bottom plate was coated overnight at 4° C. with polyethylene glycol-precipitated purified Sindbis virus antigen at a final concentration of 0.15 μg in 50 μl PBS. Control wells were incubated with PBS lacking Sindbis virus antigen. Wells were blocked with 100 ul PBS/5% BSA at room temperature for one hour, washed three times with PBS/1% Tween-20 buffer, and then incubated with serial dilutions of primary antibodies (range 1.1–90 ng/ml): purified recombinant R6 IgG, purified R6 ascites, or S58 (a control anti-herpes virus MAb) in 50 μl working buffer (PBS/2% BSA/0.1% Tween-20) at 37° C. for 90 minutes. The plate was washed five times and then incubated with peroxidase conjugated anti-mouse IgG (1:800) in 50 μl working buffer. The colorimetric reaction was developed by adding 100 μl of substrate (4 mg o-phenylenediamine dihydrochloride, 10 μl 30% $H_2O_2$ in 10 ml citrate buffer, pH5). Absorbance at 492 nM was measured in a Titertek Multiscan; results are presented as the mean O.D. of triplicate wells.

Animal Experiments

Four-to six-week old immunodeficient scid/CB17 mice or immunocompetent Balb/c mice of either sex were used. Mice were anesthetized with methoxyflurane and inoculated intracerebrally (i.c.) with virus diluted in 0.03 cc of Hanks Balanced Salt Solution (HBSS). For antibody protection studies, Balb/c mice were infected with 10 $LD_{50}$ (20 pfu) of neuroadapted Sindbis virus (NSV) and observed for paralysis and death for 21 days. To test the ability of antibodies to protect when administered post-exposure, mice were injected with a single dose of 100 μg of either R6 from ascites or recombinant R6 or with HBSS as a control 24 hours after NSV inoculation (5 mice per treatment group). To test the abilities of antibodies to protect when administered pre-exposure, mice were injected with 100 μg of R6 from ascites or recombinant R6 24 or HBSS hours before NSV inoculation (5 mice per treatment group). For viral clearance experiments, scid/CB17 mice were infected with $10^3$ PFUs of wild-type Sindbis virus, strain AR339, and four days after infection, were treated intraperitoneally with 0.2 ml of HBSS containing 100 μg of purified recombinant R6, 100 μg purified R6 ascites, or HBSS alone (3 mice per treatment group). Four days after antibody treatment (eight days after infection), mice were sacrificed and brains were dissected and stored at −70° C. Freeze-thawed tissues were used to prepare a 10% homogenate in HBSS. The viral titers of each homogenate were determined by plaque assay titration on BHK-21 cells.

Results

Cloning and sequencing of anti-E2 MAb R6 heavy light chain genes

R6, a MAb to the Sindbis virus E2 envelope glycoprotein, is a strong neutralizing antibody that has several important antiviral properties (Olmsted et al., 1984, Olmsted et al., 1986, Schoep et al., 1993). R6 recognizes an epitope on the E2 glycoprotein that is an important determinant of viral pathogenesis and MAb R6 escape mutant viruses have attenuated neurovirulence in mice. In addition, treatment of persistently infected scid mice or cultured dorsal root ganglion neurons with MAb R6 mediates the clearance of infectious virus by restricting viral gene expression (Levine et al., 1991). Other MAbs, to the same epitope recognized by MAb R6, have also been shown to protect mice against fatal encephalitis.

Figure 1B:
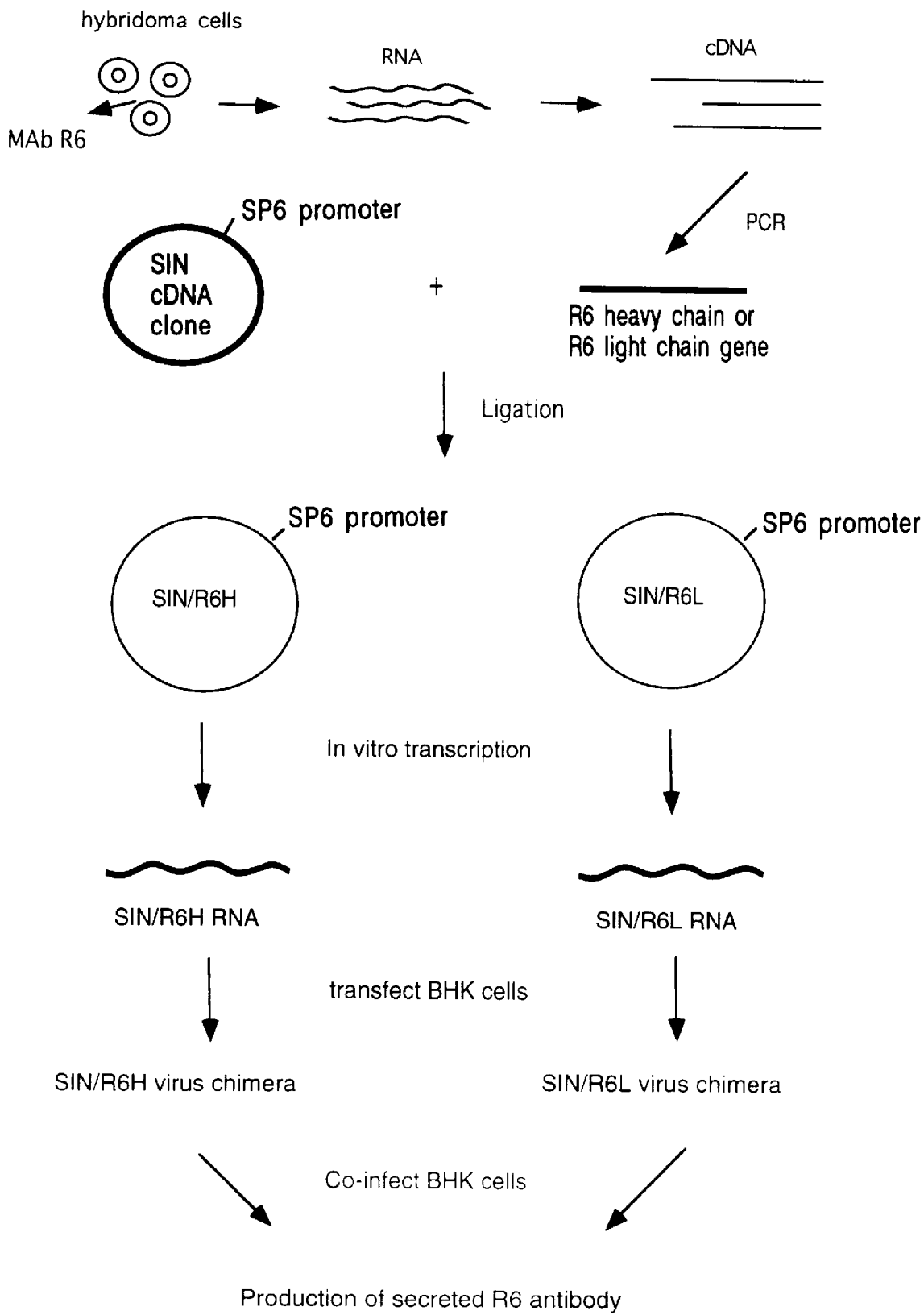

To further understand the mechanism by which R6 functions as an antiviral antibody, a strategy was devised to express native R6 antibodies in Sindbis virus-infected cells (FIGS. 1A and 1B). As a first step, the rearranged variable region genes, VH and VL were cloned and sequenced, from R6 hybridoma cDNA. VH and VL genes were amplified by PCR using degenerate forward primers that hybridize to the relatively conserved leader sequences (Coloma et al. 1992) and a set of degenerate reverse primers for the J region of mouse VH and $V_K$. PCR-amplified VH and VL genes were cloned into pCR™ and sequenced as described in the Materials and Methods. The cDNA and encoded amino acid sequences of R6 VH and $V_K$ are shown in FIGS. 2A and 2B.

Construction of recombinant Sindbis virus/Ig

After determining the sequences of R6 VH and VL genes, the entire rearranged heavy chain and light chain genes were cloned into the Sindbis virus cDNA clone, dsTE12. The R6 heavy light chain cDNAs were inserted downstream of a duplicated internal promoter and upstream of the Sindbis virus 3' nontranslated region to generate two plasmids, Sindbis virus/R6H and Sindbis virus/R6L. Both heavy light chain genes retained the 5' hydrophobic leader sequences to ensure protein trafficking to the secretory pathway. The recombinant Sindbis virus/R6 RNA's were transcribed from cDNA templates by in vitro transcription and were subsequently transfected into BHK-21 cells to yield infectious Sindbis virus/R6H and Sindbis virus/R6L chimeric virus stocks. The titers of viral stocks collected from the supernatant of infected cells ranged between $10^7$ to $10^9$ pfu/ml.

Intracellular expression of R6 by recombinant Sindbis virus chimeras

The ability of Sindbis virus/R6H and Sindbis virus/R6L to express heavy light chain proteins in mammalian cells was examined by immunofluorescent staining with an anti-mouse IgG-Fc or anti-mouse κ chain antibody, respectively. Cells infected with Sindbis virus/R6H and cells infected with Sindbis virus/R6L both demonstrated a cytoplasmic vesicular pattern of immunoreactivity, which is typical for secretory proteins (FIGS. 3A and 3B). Virtually 100% of cells infected with Sindbis virus/R6L or with Sindbis virus/R6H expressed light or heavy chain proteins, respectively, as demonstrated using a two color immunofluorescence assay to simultaneously detect Sindbis virus proteins and light chains or heavy chains. These experiments indicate that Sindbis virus/R6H and Sindbis virus/R6L express heavy light chain proteins in virally-infected BHK cells.

Secretion of assembled R6 heavy light chain antibody molecules

Figure 4:
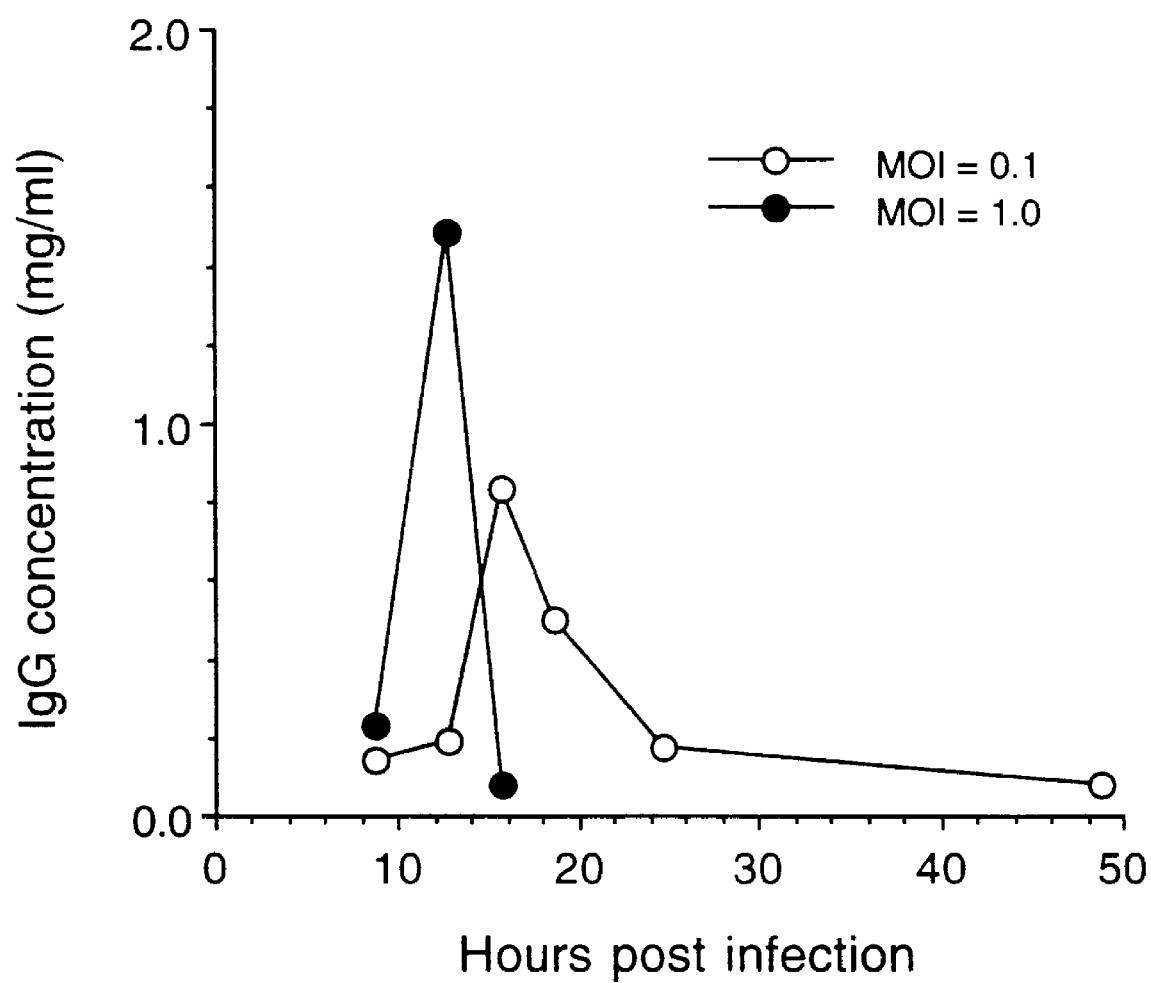

To produce secreted recombinant R6 native antibodies, BHK-21 cells were cotransfected with Sindbis virus/R6H and Sindbis virus/R6L virus chimeras at an MOI of 0.1 or 1 in DMEM supplemented with 1% fetal bovine serum. Supernatants were collected at serial time points after infection and purified through a staphylococcus protein A/G column. The IgG concentration in the supernatant varied as a function of MOI and time after infection; the highest level of IgG was 1.4 mg/ml in the protein A/G-purified supernatant collected 12 hours after infection at a MOI of 1 (FIG. 4). The decline in secreted IgG at later time points is a reflection of cell death that occurs within 12–24 hours (depending upon the MOI) after Sindbis virus infection of BHK cells. A similar peak yield (1.4 mg/ml) of recombinant R6 IgG production after BHK-21 cell co-infection with Sindbis virus/R6H and Sindbis virus/R6L chimeras was also observed using serum-free conditions.

Figure 5:
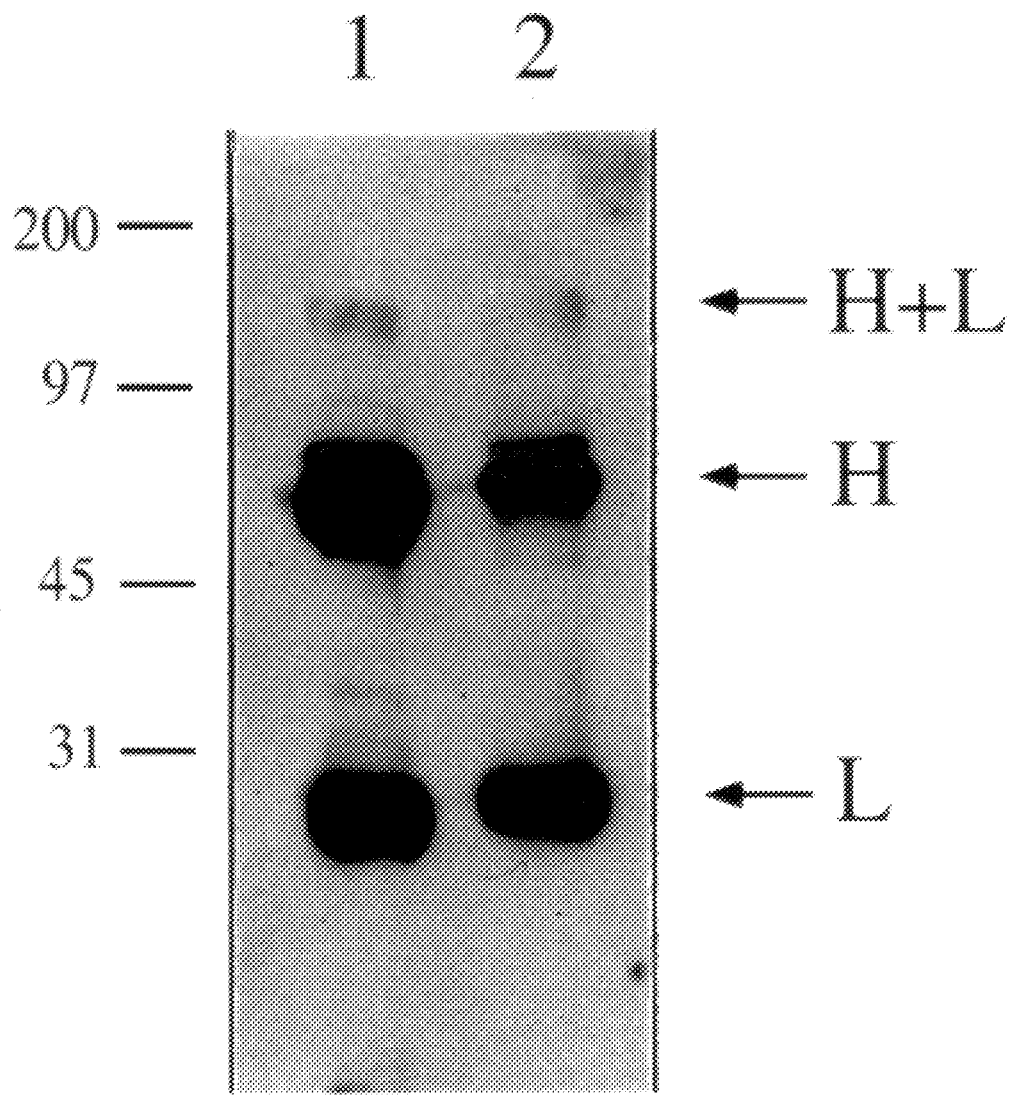

To demonstrate the assembly secretion of R6 heavy light chain proteins, Western blot analysis was performed on protein A/G-purified supernatants from BHK cells coinfected with Sindbis virus/R6L and Sindbis virus/R6H. Using anti-mouse IgG γ anti-mouse κ antibodies, recombinant R6 was found to contain a 53 kd and a 27 kd proteins, which are equivalent in molecular weight to the heavy chain and light chain proteins, respectively, of R6 IgG purified from ascites (FIG. 5). Since protein A/G binds the Fc portion of the heavy chain constant region and does not bind to light chain, the presence of both light chains and heavy chains in the protein A/G-purified supernatant of coinfected cells is evidence for the secretion of an assembled native R6 antibody.

Secreted recombinant R6 is biologically similar to the authentic R6

Figure 6:
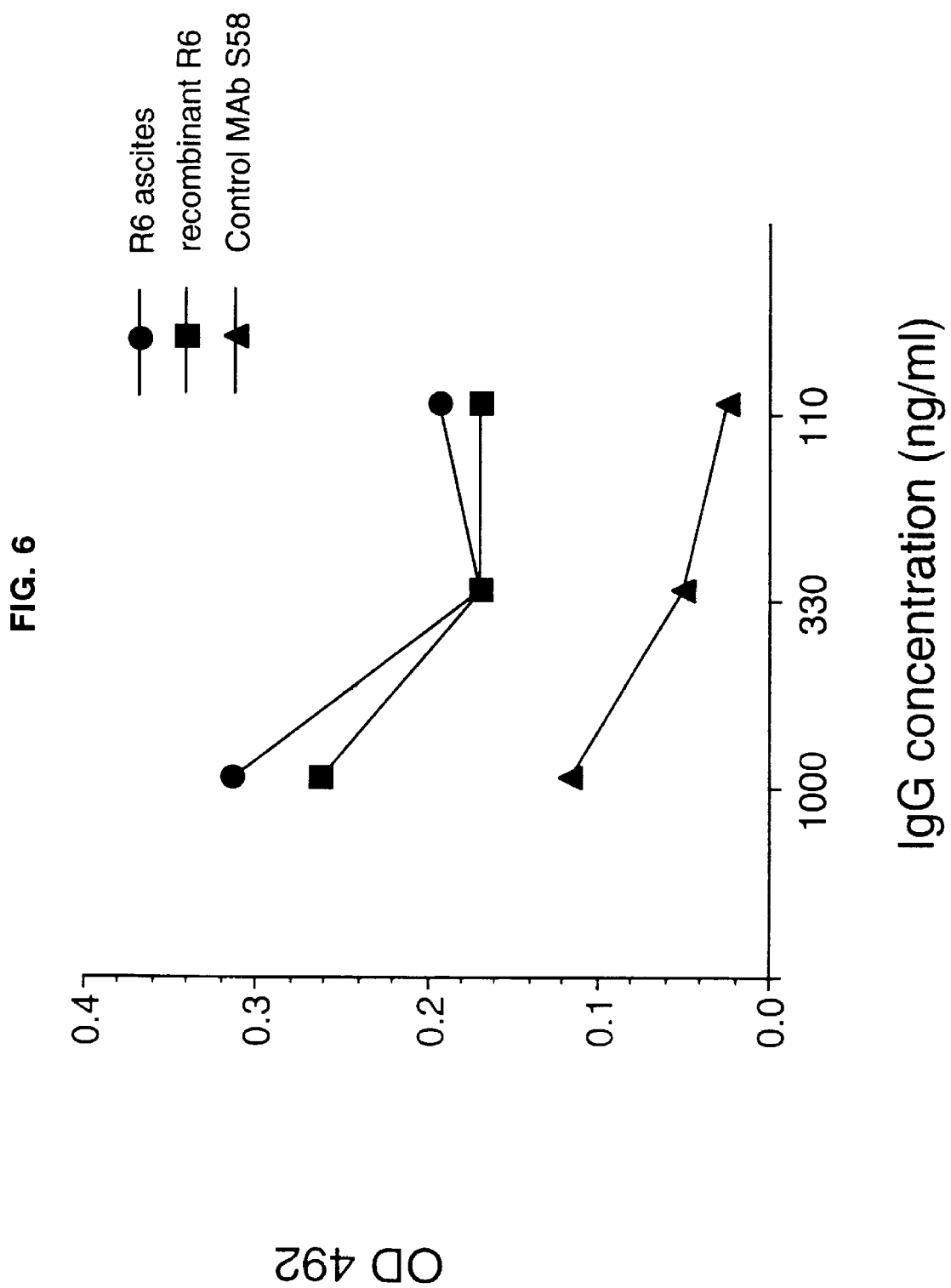

After demonstrating that co-infection of BHK cells with Sindbis virus/R6L and Sindbis virus/R6H results in a high yield of secreted recombinant R6, the biological activity was investigated to determine whether recombinant R6 is similar to MAb R6 from ascites fluid. First, the immunoreactivity to purified Sindbis virus antigen in an ELISA was measured. The ELISA reactivity of recombinant R6 was similar to that of R6 from ascites fluid (FIG. 6), whereas no reactivity was detected with a control anti-herpes virus antibody. Thus, the Sindbis virus binding activity of recombinant R6 resembles authentic R6.

To determine whether recombinant R6 functions as an antiviral antibody in vivo, the effects of recombinant R6 treatment on defined stages of Sindbis virus pathogenesis was investigated. Monoclonal antibodies to the E2 envelope glycoprotein are known to protect mice against fatal encephalitis caused by a neuroadapted strain of Sindbis virus, NSV (Stanley et al., 1986). The panel of MAbs that protect against disease after prophylactic administration is overlapping, but different from the panel of MAbs that protect against disease after post-exposure administration, suggesting distinct mechanisms by which antibodies are effective in the prophylaxis and post-exposure period. The ability of recombinant R6, R6 from ascites fluid, and a control, non-protective anti-E2 MAb, 202, to prevent death due to NSV was compared when administered either 24 hours before or 24 hours after infection. NSV infection resulted in 100% mortality in 4–6 week old Balb/c mice which was not reduced by pre-or post-exposure treatment with the anti-E2 MAb 202. In contrast, the treatment of Balb/c mice either 24 hours before virus infection or 24 hours after virus infection with either 100 μg of recombinant R6 or R6 derived from ascites fluid completely prevented mortality due to NSV infection.

Figure 7:
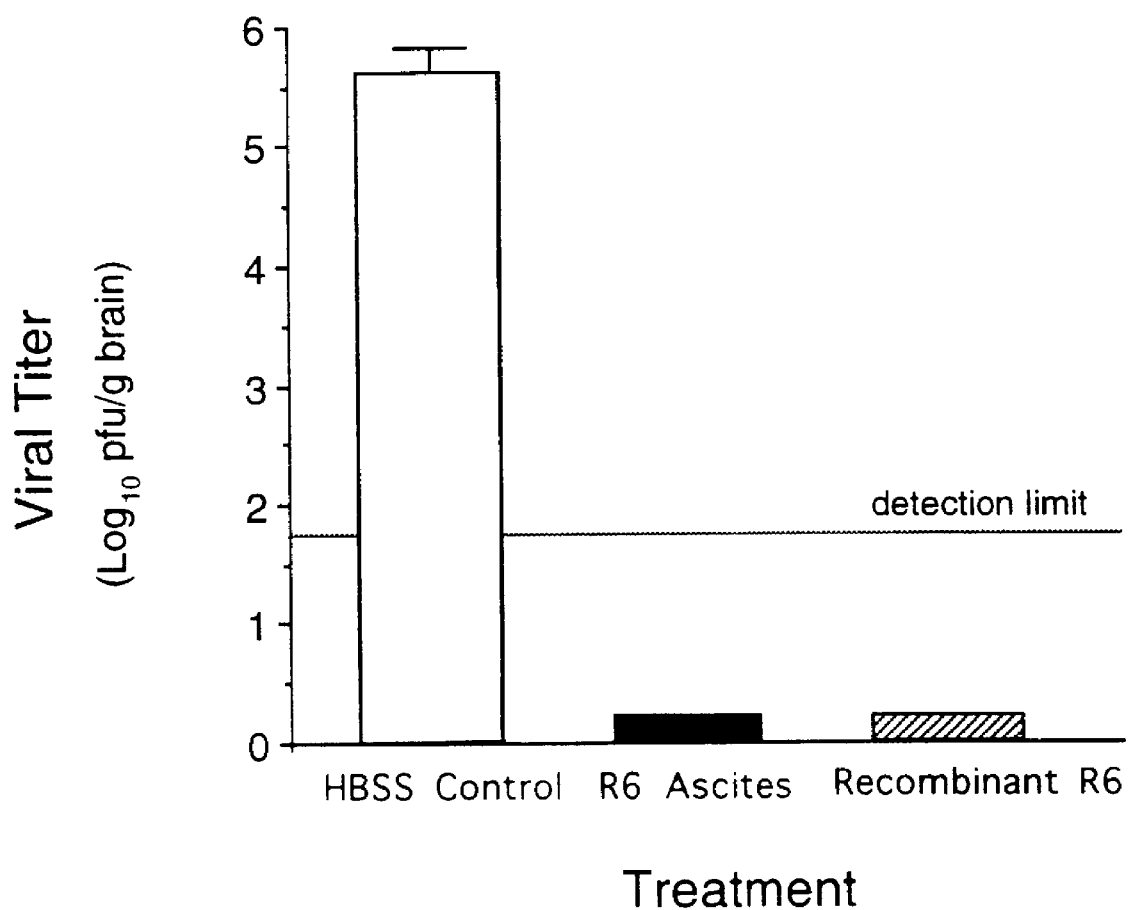

In addition to protecting against fatal disease caused by NSV, anti-E2 MAbs play a critical role in mediating recovery from nonfatal disease. Unlike NSV, wild-type Sindbis virus produces an acute self-limited asymptomatic illness in immunocompetent weanling mice. Scid mice, that lack specific cellular and humoral immune responses, develop a persistent infection that can be cleared by the administration of MAbR6 and other anti-E2 MAbs (Levine et al, 1991). To determine whether recombinant R6 also mediates viral clearance, the ability of recombinant R6, R6 from ascites, and HBSS to clear infectious virus from the brains of persistently infected scid mice was compared (FIG. 7). Four days after treatment with either recombinant R6 or R6 from ascites, no infectious virus could be detected in brain homogenates. In contrast, greater than $10^5$ PFU/g brain were present in the brains of scid mice treated with HBSS. These results indicate that recombinant R6 mediates viral clearance as effectively as R6 ascites. Taken together with the results in NSV protection studies, the antiviral activity in vivo of recombinant R6 is indistinguishable from that of hybridoma-derived R6.

Discussion

Double subgenomic Sindbis virus vectors were used to coexpress heavy light chains genes of an antiviral antibody, R6, in mammalian cells. The results demonstrate that coinfection of BHK cells with chimeric Sindbis virus/R6 light chain and Sindbis virus/R6 heavy chain viruses leads to the secretion of assembled native antibody. The secreted recombinant antibody demonstrates both in vitro binding and in vivo antiviral activity that is identical to the authentic, hybridoma-derived antibody. Thus, the Sindbis virus vector system represents a tool to produce genetically engineered biologically active antibodies.

Sindbis virus has been used previously as a vector for the expression of high levels of heterologous proteins, including bacterial chloramphenicol acetyltransferase (CAT) (Xiong et al., 1989), influenza hemagglutinin protein (Hahn et al., 1992), insulin-regulated glucose-transporter protein (Piper et al., 1992), Bcl-2 and related family members (Cheng et al., 1996, Levine et al., 1996) and a ScFV antibody against tick borne encephalitis virus (Jiang et al., 1994, Jiang et al. 1995). Because of the toxicity of Sindbis virus for mammalian cells, it is only useful for transient expression. However, as a transient expression system, it has several important advantages. Because Sindbis virus replicates to high levels and interferes with host cell functions, very large amounts of heterologous protein can be expressed within hours after infection. The steps required to generate infectious RNA vectors, including the genetic manipulation of full-length Sindbis virus cDNAs, in vitro RNA transcription, and RNA transfection, are straightforward. Perhaps most importantly, because Sindbis virus is a positive strand RNA virus that replicates exclusively in the cytoplasm, cDNAs can be cloned directly into Sindbis virus vectors and there is no possibility of adventitious splicing.

The Sindbis virus vector system offers an important additional unique advantage with respect to the expression of recombinant antibodies. In this study, the feasibility of the strategy of coinfecting cells with different Sindbis virus vectors to produce functional multimeric proteins is demonstrated. These findings suggest that the Sindbis virus vector system may be ideally suited for structure-function studies involving the production of antibody variants that contain different combinations of heavy light chains or that contain different desired mutations.

A similar dual infection protocol has been used with vaccinia virus vectors to express heavy light chains that associate to form secreted functional antibody (Carroll et al., 1992). In the vaccinia virus system, cDNAS are transfected into vaccinia virus-infected cells, recombinant viruses are selected for after several days growth in culture and then screened for antibody production. Compared to the vaccinia virus expression system, recombinant Sindbis virus expression vectors can be constructed more rapidly, since foreign cDNAs are cloned directly into Sindbis virus vectors which serve as a template for generating infectious RNA.

A potential limitation of dual infection strategies to produce recombinant antibodies is that it may not be possible to co-infect all cells with both virus vectors. Depending upon the multiplicity of infection (i.e. ratio of infectious virus particles/cell), between 25–50% of cells were coinfected with light chain and heavy chain vectors. Similar findings were also observed by Carroll et al. using the vaccinia virus expression system. Although the conditions used were sufficient to generate high yields of secreted antibody, conditions which resulted in more than 50% of cells co-infected with light chain and heavy chain-expressing virus vectors were unable to be defined. Therefore, the strategy that was used may not be suitable for applications involving the production of native antibodies targeted to intracellular compartments. Furthermore, given that inserts of greater than 2 kb tend to be unstable in the Sindbis virus genome, it would not be practical to express full-length heavy light chains in tandem in a Sindbis virus vector. The envelope of the Sindbis virus would be unable to package properly transcripts derived from Sindbis viral vectors containing inserts greater than 2 kb. One could not coinfect the eukaryotic host cell with a chimeric Sindbis vector containing an insert of immunoglobulin genes in tandem due to inability to package properly the resulting RNA. Based upon these considerations, the use of Sindbis virus as a vector for the expression of intracellular antibodies may be limited to scFv's or antibody fragments because the Sindbis viral vector would be unable to express the fully assembled antibody intracellularly.

Although an antiviral antibody containing mouse heavy light chains was constructed, the Sindbis virus vector system could easily be adapted to produce chimeric, humanized or human antibodies. The feasibility of producing high yields of humanized biologically active antibodies suggests that the Sindbis virus vector system may be useful for the generation of therapeutic antibodies. Results demonstrate that an antibody produced using the Sindbis virus vector system is able to protect mice against a lethal infection of the central nervous system. The Sindbis virus vector system may also be useful to produce recombinant antibodies that replace immunoglobulin therapies that are presently being used in the treatment of certain inflammatory disorders, immunodeficiency states, and viral infections. The advantages of such recombinant antibodies (versus serum immunoglobulin therapy MAbs derived from mouse hybridoma cells) would be that they can easily be humanized. Further these antibodies can be custom designed to modify their specificity, and produced in very large quantities.

In summary, these results demonstrate that the co-infection of BHK cells with chimeric Sindbis viruses expressing heavy chain and light chains results in the secretion of an anti-Sindbis virus E2 envelope glycoprotein antibody that has potent antiviral activities in vivo. One can exploit this expression system to make genetic modifications in the anti-E2 MAb, R6, that will permit a more detailed investigation of the molecular determinants of anti-E2 antibody-E2 protein interactions. In addition, the Sindbis virus vector antibody expression system is likely to be useful for the rapid production of high yields of recombinant antibodies for other research or therapeutic applications.

REFERENCES

1. Bowdish K., Tang Y., Hicks J. B. and Hilvert D. (1991) "Yeast expression of a catalytic antibody with chorismate mutase activity." *J. Biol. Chem.* 266: 11901–11908.
2. Carrol A. R., Rowlands D. J. and Clarke B. E. (1992) "Synthesis and secretion of a functional antibody in a vaccinia virus expression system." *Molecular Immunol.* 29:821–827.
3. Coloma M. J., Hastings A., Wims L. A. and Morrison S. L. (1992) "Novel vector for the expression of antibody molecules using variable regions generated by polymerase chain reaction." *J. Immunol. Methods* 152:89–104.
4. Cheng, E. H.-Y., et al., (1996) "Bax-independent Inhibition of Apoptosis By Bcl-X." *Nature* 379:554–556.
5. Hasemann C. A. and Capra J. D. (1990) "High level production of a functional immunoglobulin heterodimer in a baculovirus expression system." *Proc. Natl. Acad. Sci USA* 87:3942–3946.
6. Hahn C. S., Hahn Y. S., Braciale T. J. and Rice C. M. (1992) "Infectious Sindbis virus transient expression vectors for studying antigen processing and presentation." *Proc. Natl. Acad. Sci. USA* 89: 2679–2683.
7. Hertz J and Huang H. V. (1992) "Utilization of Heterologous Alphavirus Junction Sequences as Promoters by Sindbis Virus" *J. Virol* 66: 491–496.
8. Horwitz A. H., Chang C. P., Better M., Hellstrom K. E. and Bobinson R. R. (1988) "Secretion of functional antibody Fab fragment from yeast cells." *Proc. NatlAcad. Sci. USA* 85:8678–8682.
9. U.S. Pat. No. : 5,217,879, issued Jun. 8, 1993 to Huang H. V., Levis R., Rice C. M., Schlesinger S., Shen P., Xiong C.
10. Huse W. D., Sastry L., Iverson S. A., Kang A. S., Alting-Mees M., Burton D. R., Benkovic S. J. and Lerner R. (1989) "Generation of a large combinatorial library of the immunoglobulin repertoire in phage lambda." *Science* 246: 1275–1281.

11. Jiang W., Bonnert T. P., Venugopal K. and Gould E. A. (1994) "A single chain antibody fragment expressed in bacteria neutralizes tick-borne Flaviviruses." *Virology* 200:21–28.
12. Jiang W., Venugopal K. and Gould E. A. (1995) "Intracellular interference of tick-borne flavivirus infection by using a single-chain antibody fragment delivered by recombinant Sindbis virus." *J. Virol* 69:1044–1049.
13. Johnson R. T., McFarland H. F. and Levy S. E. (1972) "Age-dependent resistance to virus encephalitis: studies of infections due to Sindbis virus in mice" *J. Infect Dis.* 125:257–262.
14. Jackson A. C., Moench T. R., Griffin D. E., Johnson R. T. (1988) "The pathogenesis of spinal cord involvement in the encephalomyelitis of mice caused by neuroadapted Sindbis virus infection." *Lab. Invest.* 56:418–423.
15. Levine B., Hardwick J. M., Trapp B. D., Crawford T. O., Bollinger R. C. and Griffin D. E. (1991) "Antibody-mediated clearance of alphavirus infection from neurons." *Science* 254:856–860.
16. Levine B., Goldman J., Jiang H. H., Griffin D. E. and Hardwick J. M. (1996) "Bcl-2 protects mice against fatal alphavirus encephalitis." *Proc. Natl. Acad. Sci. USA* 93:4810–4815.
17. Nesbit M., Fu Z. F., McDonald-Smith J., Steplewski Z. and Curtis P. J. (1992) "Production of a functional monoclonal antibody recognizing human colorectal carcinoma cells from a baculovirus expression system." *J. Immunol. Method* 151:201–208.
18. Olmsted R. A., Baric R. S., Sawyer B. A., Johnston R. E. (1984) "Sindbis virus mutants selected for rapid growth in cell culture display attenuated virulence in animals." *Science.* 225:424–427,
19. Olmsted R. A., Meyer W. J., Johnston R. E. (1986) "Characterization of Sindbis virus epitopes important for penetration in cell culture and pathogenesis in animals." *Virol.* 148:245–254.
20. Piper R. C., Tai C., Slot J. W., Hahn C. S., Rice C. M. Huang H. and James D. E. (1992) "The efficient intracellular sequestration of the insulin-regulatable glucose transporter (GLUT-4) is conferred by the $NH_2$ terminus." *J. Cell Biol.* 117: 729–743.
21. Pluckthun A. (1990) "Antibodies from Escherichia coli." *Nature* 347:497–498.
22. Poul M. A., Cerutti, M., Chaabihi H., Ticchioni M., Deramoudt F. X., Bernard A., Devauchelle G., Kaczorek M., Lefranc M. P. (1995) "Cassette baculovirus vectors for the production of chimeric, humanized, or human antibodies in insect cells." *Eur. J. Immunol.* 25:2005–2009.
23. Sambrook J., Fritsch E. F., Maniatis T. (1989) *Molecular Cloning: a laboratory manual, Second Edition.* Cold Spring Harbor Laboratory Press.
24. Sastry L., Alting-Mees M., Huse W. D., Short J. M., Sorge J. A., Hay B. N. Janda K. D., Benkovic S. J., Lerner R. A. (1989) "Cloning of the immunological repertoire in Escherichia coli for generation of monoclonal catylytic antibodies: construction of a heavy chain variable region-specific cDNA library." *Proc. Natl. Acad. Sci. USA* 86:5728–5732.
25. Schlesinger S. (1993) "Alphaviruses—vectors for the expression of heterologous genes." *TIBTECH* 11: 18–22.
26. Schmaljohn A. L., Johnson E. D., Dalrymple J. M., Cole G. A. (1982) "Non-neutralizing monoclonal antibodies can prevent lethal alphavirus encephalitis." *Nature* 297:70–72.
27. Schoepp R. J., Johnston R. E. (1993) "Directed mutagenesis of a Sindbis virus pathogenesis site." *Virology* 193:149–159.
28. Skerra A. and Pluckthun A. (1988) "Assembly of a functional immunoglobulin Fv fragment in Escherichia coli." *Science* 240:1038–1041.

29. Stanley J., Cooper S. J., Griffin D. E. (1986) "Monoclonal antibody cure and prophylaxis of lethal Sindbis virus encephalitis in mice" *J. Virol* 58:107–115.

30. Strauss E. G. and Strauss J. H. (1986) "The Togaviridae and Flaviviridae" (Schlesinger S. and Schlesinger M. J. eds.). pp. 35–90. Plenum, N.Y.

31. Ubol S., Levine B, Lee S. H., Greenspan N. S., Griffin D. E. (1995) "Roles of immunoglobulin valency the heavy-chain constant domain in antibody-mediated downregulation of Sindbis virus replication in persistently infected neurons." *J. Virol* 1995:1990–1993.

32. Xiong C., Levis R., Shen P., Schlesiger S., Rice C. M. and Huang H. V. (1989) "Sindbis virus: an effecient, broad host range vector for gene expression in animal cells." *Science* 243: 1188–1191.

33. Ward S. E., Gussow D., Griffiths A. D., Jones P. T., Winter G. (1989) "Binding activities of a repertoire of single immunoglublin variable domains secreted from Escherichia coli." *Nature* 341: 544–546.

---

What is claimed is:

1. A method of producing a chimeric Sindbis virus expressing immunoglobulin heavy chain protein which comprises:

(a) obtaining the nucleic acid which encodes immunoglobulin heavy chain protein;

(b) operatively linking the obtained nucleic acid to a Sindbis virus cDNA clone which contains all the elements, including structural genes, required for viral replication and transcription so as to form a chimeric Sindbis virus cDNA clone;

(c) transcribing the chimeric Sindbis virus cDNA clone of step (b);

(d) isolating the transcript of step (c);

(e) transfecting the isolated transcripts of step (d) into a eukaryotic cell in vitro; and (f) culturing the cell of step (e) so as to produce a chimeric Sindbis virus expressing immunoglobulin heavy chain protein.

2. The method of claim 1, wherein the obtaining of step (a) comprises:

(i) obtaining hybridoma cells expressing a specific monoclonal antibody, (ii) isolating mRNAs from said hybridoma cells, (iii) generating cDNAs of the isolated mRNAs from step (ii), and (iv) isolating cDNAs encoding immunoglobulin heavy chain protein so as to obtain a nucleic acid which encodes immunoglobulin heavy chain protein.

3. The method of claim 2, wherein the isolation of cDNAs encoding immunoglobulin heavy chain protein of step (iv) comprises amplifying the cDNAs generated in step (iii) and detecting the presence of cDNAs encoding immunoglobulin heavy chain protein.

4. A chimeric Sindbis virus expressing immunoglobulin heavy chain protein and produced by the method of claim 1.

5. A method of producing a chimeric Sindbis virus comprising a nucleic acid molecule expressing immunoglobulin light chain protein which comprises:

(a) obtaining the nucleic acid which encodes immunoglobulin light chain protein;

(b) operatively linking the obtained nucleic acid to a Sindbis virus cDNA clone which contains all the elements, including structural genes, required for viral replication and transcription so as to form a chimeric Sindbis virus cDNA clone;

(c) transcribing the chimeric Sindbis virus cDNA clone of step (b);

(d) isolating the transcript of step (c);

(e) transfecting the isolated transcripts of step (d) into a eukaryotic cell in vitro; and (f) culturing the cell of step (e) so as to produce a chimeric Sindbis virus expressing immunoglobulin light chain protein.

6. The method of claim 5, wherein the obtaining of the nucleic acids of step (a) comprises:

(i) obtaining hybridoma cells expressing a specific monoclonal antibody, (ii) isolating mRNAs from the said hybridoma cells, (iii) generating cDNAs of the isolated mRNAs from step (ii), and (iv) isolating cDNAs encoding immunoglobulin light chain protein so as to obtain a nucleic acid which encodes immunoglobulin light chain protein.

7. The method of claim 6, wherein the isolation of cDNAs encoding immunoglobulin light chain protein of step (iv) comprises amplifying the cDNAs generated in step (iii) and detecting the presence of cDNAs encoding immunoglobulin light chain protein.

8. A chimeric Sindbis virus expressing immunoglobulin light chain protein and produced by the method of claim 5.

9. A method of expressing a biologically active recombinant antibody which comprises:

(a) obtaining nucleic acids which encode immunoglobulin light chain protein and heavy chain protein;

(b) operatively linking the obtained nucleic acids to Sindbis virus cDNA clones which contain all the elements, including structural genes, required for viral replication and transcription so as to form chimeric Sindbis virus cDNA clones, wherein at least one clone comprises the nucleic acid encoding immunoglobulin heavy chain and at least another clone comprises the nucleic acid encoding immunoglobulin light chain;

(c) transcribing the chimeric Sindbis virus cDNA clones of step (b);

(d) isolating the transcripts from step (c);

(e) transfecting the isolated transcripts of step (d) into a eukaryotic cell in vitro;

(f) culturing the transfected cell of step (e) so as to produce chimeric Sindbis viruses, wherein at least one virus comprises the nucleic acid encoding immunoglobulin heavy chain protein and at least another virus comprises the nucleic acid encoding immunoglobulin light chain protein;

(g) isolating the viral vectors of step (f);

(h) coinfecting a host cell in vitro, with the isolated viral vectors of step (g) under conditions so that the cell expresses biologically active recombinant antibodies.

10. The method of claim 9, wherein the host cell is a mammalian cell.

11. The method of claim 9, wherein the host cell is from an arthropod.

12. An expression cell line that produces biologically active recombinant antibodies comprising the chimeric Sindbis virus of claim 4 and the chimeric Sindbis virus of claim 8.

* * * * *

SEQUENCE LISTING ( 1 ) GENERAL INFORMATION:

( i i i ) NUMBER OF SEQUENCES: 33

( 2 ) INFORMATION FOR SEQ ID NO:1:

( i ) SEQUENCE CHARACTERISTICS:
( A ) LENGTH: 390 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:1:

ATGGATTTTC AAGTGCAGAT TTTCAGCTTC CTGCTAATCA GTGTCACAGT CATAATGTCC 60

```
AGAGGAGAAA  ATGTGCTCAC  CCAGTCTCCA  GCAATAATGG  CTGCCTCTCT  GGGGCAGAAG       120

GTCACCATGA  CCTGCAGTGC  CAGCTCAAGT  GTAAGTTCCA  GTTACTTGCA  CTGGTACCAG       180

CAGAAGTCAG  GCGCTTCCCC  CAAACCCTTG  ATTCATAGGA  CATCCAACCT  GGCTTCTGGA       240

GTCCCAGCTC  GCTTCAGTGG  CAGTGGGTCT  GGGACCTCTT  ACTCTCTCAC  AATCAGCAGC       300

GTGGAGGCTG  AAGATGATGC  AACTTATTAC  TGCCAGCAGT  GGAGTGGTTA  CCCATTCACG       360

TTCGGTGCTG  GGACCAAGCT  GGAGCTGAAA                                           390
```

(2) INFORMATION FOR SEQ ID NO:2:

(i) SEQUENCE CHARACTERISTICS:
        (A) LENGTH: 130 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Met  Asp  Phe  Gln  Val  Gln  Ile  Phe  Ser  Phe  Leu  Leu  Ile  Ser  Val  Thr
 1              5                        10                       15
Val  Ile  Met  Ser  Arg  Gly  Glu  Asn  Val  Leu  Thr  Gln  Ser  Pro  Ala  Ile
              20                        25                       30
Met  Ala  Ala  Ser  Leu  Gly  Gln  Lys  Val  Thr  Met  Thr  Cys  Ser  Ala  Ser
              35                        40                       45
Ser  Ser  Val  Ser  Ser  Ser  Tyr  Leu  His  Trp  Tyr  Gln  Gln  Lys  Ser  Gly
        50                       55                       60
Ala  Ser  Pro  Lys  Pro  Leu  Ile  His  Arg  Thr  Ser  Asn  Leu  Ala  Ser  Gly
 65                       70                       75                       80
Val  Pro  Ala  Arg  Phe  Ser  Gly  Ser  Gly  Ser  Gly  Thr  Ser  Tyr  Ser  Leu
                   85                       90                       95
Thr  Ile  Ser  Ser  Val  Glu  Ala  Glu  Asp  Asp  Ala  Thr  Tyr  Tyr  Cys  Gln
                 100                      105                      110
Gln  Trp  Ser  Gly  Tyr  Pro  Phe  Thr  Phe  Gly  Ala  Gly  Thr  Lys  Leu  Glu
                 115                      120                      125
Leu  Lys
     130
```

(2) INFORMATION FOR SEQ ID NO:3:

(i) SEQUENCE CHARACTERISTICS:
        (A) LENGTH: 423 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
ATGGAATGGA  GCTGGGTCTT  TATCTTTCTC  TTGTCAGTAA  CTGCAGATGT  CCACTCCCAG        60

GTCCAGTTGC  AGGAGTCTGG  AGGTGAGCTG  GTAAGGCCTG  GGACTTCAGT  GAAGATATCC       120

TGCAAGGCTT  CTGGCTACAC  CTTCACTAAT  TACTGGCTAG  GTTGGGTAAA  GCAGAGGCCT       180

GGACATGGAC  TTGAGTGGAT  TGGAGATATT  TACCCTGGAG  GTGATTATAC  TAATTACAAT       240

GAGAAGTTCA  AGGGCAAGGC  CACACTGACT  GCAGACACAT  CCTCCAGCAC  TGCCCACATG       300

CAGCTCAGTA  GCCTGACATC  TGAGGACTCT  GCTGTCTATT  TCTGTGCAAT  ATTTCATTAC       360

TCCGGCTACA  GGTACTTCGA  TGTCTGGGGC  GCAGGGACCA  CGGTCACCGT  CTCCTCAGCT       420

AGC                                                                         423
```

( 2 ) INFORMATION FOR SEQ ID NO:4:

( i ) SEQUENCE CHARACTERISTICS:
        ( A ) LENGTH: 141 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Met Glu Trp Ser Trp Val Phe Ile Phe Leu Glu Ser Val Thr Ala Asp
 1               5                  10                  15
Val His Ser Gln Val Gln Leu Gln Glu Ser Gly Gly Glu Leu Val Arg
            20                  25                  30
Pro Gly Thr Ser Val Lys Ile Ser Cys Lys Ala Ser Gly Tyr Thr Phe
        35                  40                  45
Thr Asn Tyr Trp Leu Gly Trp Val Lys Gln Arg Pro Gly His Gly Leu
    50                  55                  60
Glu Trp Ile Gly Asp Ile Tyr Pro Gly Gly Asp Tyr Thr Asn Tyr Asn
65                  70                  75                  80
Glu Lys Phe Lys Gly Lys Ala Thr Leu Thr Ala Asp Thr Ser Ser Ser
                85                  90                  95
Thr Ala His Met Gln Leu Ser Ser Leu Thr Ser Glu Asp Ser Ala Val
            100                 105                 110
Tyr Phe Cys Ala Ile Phe His Tyr Ser Gly Tyr Arg Tyr Phe Asp Val
        115                 120                 125
Trp Gly Ala Gly Thr Thr Val Thr Val Ser Ser Ala Ser
130                 135                 140
```

( 2 ) INFORMATION FOR SEQ ID NO:5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other Nuclic Acid ( x i ) SEQUENCE DESCRIPTION: SEQ ID NO:5:

GGTGCTGGGA CCAAGCTGGA GCTGAAA                                     27

( 2 ) INFORMATION FOR SEQ ID NO:6:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:6:

CACCTCCGTG GTTCGACCTT TAGTTTGCAT TCAGCTGTCT                     40

( 2 ) INFORMATION FOR SEQ ID NO:7:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear (  i i ) MOLECULE TYPE: Other Nucleic Acid ( x i ) SEQUENCE DESCRIPTION: SEQ ID NO:7:

TGGACGTTCG GTGGAGGCAC CAAGCTGGAA ATCAAACGTA AGTAGAA 47

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Trp Thr Phe Gly Gly Gly Thr Lys Leu Glu Ile Lys
1               5                       10

( 2 ) INFORMATION FOR SEQ ID NO:9:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:9:

CTCCCCCCTG GTTCGACCTT TATTTTGCAT TCAGCTG 37

( 2 ) INFORMATION FOR SEQ ID NO:10:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:10:

TACACGTTCG GAGGGGGGAC CAAGCTGGAA ATAAAACGTA AGTAGTC 47

( 2 ) INFORMATION FOR SEQ ID NO:11:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Tyr Thr Phe Gly Gly Gly Thr Lys Leu Glu Ile Lys
1               5                       10

( 2 ) INFORMATION FOR SEQ ID NO:12:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:12:

CCGAGCCCCT GTTTCAACCT TTATTTTGCA TTCAGCTGTCT 41

( 2 ) INFORMATION FOR SEQ ID NO:13:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:13:

TTCACGTTCG GCTCGGGGAC AAAGTTGGAA ATAAAACGTA AGTAGAC 47

( 2 ) INFORMATION FOR SEQ ID NO:14:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Phe Thr Phe Gly Ser Gly Thr Lys Leu Glu Ile Lys
1               5                   10

( 2 ) INFORMATION FOR SEQ ID NO:15:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:15:

ACGACCCTGG TTCGACCTCG ACTTTGCATT CAGCTG 36

( 2 ) INFORMATION FOR SEQ ID NO:16:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:16:

CTCACGTTCG GTGCTGGGAC CAAGCTGGAG CTGAAACGTA AGTACAC 47

( 2 ) INFORMATION FOR SEQ ID NO:17:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Leu Thr Phe Gly Ala Gly Thr Lys Leu Glu Leu Lys
1               5                   10

( 2 ) INFORMATION FOR SEQ ID NO:18:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:18:

GTCCCTGGTG CCAGTGGCAG AGGAGT         26

( 2 ) INFORMATION FOR SEQ ID NO:19:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:19:

TACTGGTACT TCGATGTCTG GGGCGCAGGG ACCACGGTCA CCGTCTCCTC A         51

( 2 ) INFORMATION FOR SEQ ID NO:20:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Tyr Trp Tyr Phe Asp Val Trp Gly Ala Gly Thr Thr Val Thr Val Ser
1             5                     10                     15

Ser ( 2 ) INFORMATION FOR SEQ ID NO:21:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: Other Nucleic Acid ( x i ) SEQUENCE DESCRIPTION: SEQ ID NO:21:

GGTTCCGTGG TGAGAGTGTC AGAGGAGT         28

( 2 ) INFORMATION FOR SEQ ID NO:22:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

TACTTTGACT ACTGGGGCCA AGGCACCACT CTCACAGTCT CCTCA         45

( 2 ) INFORMATION FOR SEQ ID NO:23:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:23:

Tyr Phe Asp Tyr Trp Gly Gln Gly Thr Thr Leu Thr Val Ser Ser
1               5                   10                  15

( 2 ) INFORMATION FOR SEQ ID NO:24:

( i ) SEQUENCE CHARACTERISTICS:
  ( A ) LENGTH: 28 base pairs
  ( B ) TYPE: nucleic acid
  ( C ) STRANDEDNESS: single
  ( D ) TOPOLOGY: linear ( i i ) MOLECULE TYPE: Other Nucleic Acid ( x i ) SEQUENCE DESCRIPTION: SEQ ID NO:24:

GGTTCCCTGA GACCAGTGAC AGAGACGT                                28

( 2 ) INFORMATION FOR SEQ ID NO:25:

( i ) SEQUENCE CHARACTERISTICS:
  ( A ) LENGTH: 45 base pairs
  ( B ) TYPE: nucleic acid
  ( C ) STRANDEDNESS: single
  ( D ) TOPOLOGY: linear ( i i ) MOLECULE TYPE: Other Nucleic Acid ( x i ) SEQUENCE DESCRIPTION: SEQ ID NO:25:

TGGTTTGCTT ACTGGGGCCA AGGGACTCTG GTCACTGTCT CTGCA             45

( 2 ) INFORMATION FOR SEQ ID NO:26:

( i ) SEQUENCE CHARACTERISTICS:
  ( A ) LENGTH: 15 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:26:

Trp Phe Ala Tyr Trp Gly Gln Gly Thr Leu Val Thr Val Ser Ala
1               5                   10                  15

( 2 ) INFORMATION FOR SEQ ID NO:27:

( i ) SEQUENCE CHARACTERISTICS:
  ( A ) LENGTH: 29 base pairs
  ( B ) TYPE: nucleic acid
  ( C ) STRANDEDNESS: single
  ( D ) TOPOLOGY: linear ( i i ) MOLECULE TYPE: Other Nucleic Acid ( x i ) SEQUENCE DESCRIPTION: SEQ ID NO:27:

CAGTTCCTTG GAGTCAGTGG CAGAGGAGT                               29

( 2 ) INFORMATION FOR SEQ ID NO:28:

( i ) SEQUENCE CHARACTERISTICS:
  ( A ) LENGTH: 51 base pairs (B) TYPE: nucleic acid
    (C) STRANDEDNESS: single
    (D) TOPOLOGY: linear (ii) MOLECULE TYPE: Other Nucleic Acid (xi) SEQUENCE DESCRIPTION: SEQ ID NO:28:

TACTATGCTA TGGACTACTG GGGTCAAGGA ACCTCAGTCA CCGTCTCCTC A        51

(2) INFORMATION FOR SEQ ID NO:29:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:29:

Tyr Tyr Ala Met Asp Tyr Trp Gly Gln Gly Thr Ser Val Thr Val Ser
    1               5                   10                  15

Ser (2) INFORMATION FOR SEQ ID NO:30:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:30:

TACTAGTATC TAGAATGGAA TGGAGCTGGG TC        32

(2) INFORMATION FOR SEQ ID NO:31:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:31:

ACCTGAGGTC TAGAATGGAT TTTCAAGTGC AG        32

(2) INFORMATION FOR SEQ ID NO:32:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: Other Nucleic Acid (xi) SEQUENCE DESCRIPTION: SEQ ID NO:32:

TAACTGAATC TAGATTTACC CGGAGTCCGG GA        32

(2) INFORMATION FOR SEQ ID NO:33:

(i) SEQUENCE CHARACTERISTICS:
        (A) LENGTH: 32 base pairs
        (B) TYPE: nucleic acid
        (C) STRANDEDNESS: single ( D ) TOPOLOGY: linear ( i i ) MOLECULE TYPE: Other Nucleic Acid ( x i ) SEQUENCE DESCRIPTION: SEQ ID NO:33:

```
ACTGGACGTC    TAGAACACTC    ATTCCTGTTG    AA                                                      3 2
```